US012298290B2

(12) United States Patent
Fauvet et al.

(10) Patent No.: US 12,298,290 B2
(45) Date of Patent: May 13, 2025

(54) ISOTOPIC MARKING AND IDENTIFICATION OF LIQUIDS

(71) Applicant: IDS Group, Meyzieu (FR)

(72) Inventors: Patrice Fauvet, Lyons (FR); Valérie Migeon, Lyons (FR)

(73) Assignee: IDS Group, Meyzieu (FR)

( * ) Notice: Subject to any disclaimer, the term of this patent is extended or adjusted under 35 U.S.C. 154(b) by 805 days.

(21) Appl. No.: 17/420,320

(22) PCT Filed: Dec. 31, 2019

(86) PCT No.: PCT/EP2019/087197
§ 371 (c)(1),
(2) Date: Jul. 1, 2021

(87) PCT Pub. No.: WO2020/141179
PCT Pub. Date: Jul. 9, 2020

(65) Prior Publication Data
US 2022/0065836 A1    Mar. 3, 2022

(30) Foreign Application Priority Data

Jan. 2, 2019  (FR) ........................... 1900017

(51) Int. Cl.
*G01N 33/14*    (2006.01)

(52) U.S. Cl.
CPC .................. *G01N 33/146* (2013.01)

(58) Field of Classification Search
CPC .. G01N 33/02; G01N 33/146; G01N 33/2882; C01P 2006/88; Y10T 436/13; C07B 2200/05
See application file for complete search history.

(56) References Cited

U.S. PATENT DOCUMENTS

| 5,760,394 A | 6/1998 | Welle |
| 6,750,756 B2 | 6/2004 | Stevenson et al. |
| (Continued) | | |

FOREIGN PATENT DOCUMENTS

| CN | 106248810 A | * 12/2016 | ............. G01N 30/02 |
| DE | 10200802 | 7/2003 | |
| (Continued) | | | |

OTHER PUBLICATIONS

French Search Report dated Sep. 27, 2019 in corresponding French Application No. 1900017.
(Continued)

*Primary Examiner* — Jennifer Wecker
(74) *Attorney, Agent, or Firm* — B. Aaron Schulman, Esq.; Stites & Harbison, PLLC

(57) ABSTRACT

Method for isotopic identification, allowing, where appropriate, a liquid to be linked to a site of growth or harvest or a sub-product derived from a determined liquid, via analysis of concentration or of ratios of stable isotopes, and comparison to isotopic codes generated beforehand in a manner unique to a set of liquids issued from a site of growth, harvest or conversion. The invention also relates to a method that makes it possible to give a unique code to liquids of a site of growth, harvest or conversion, and to a computer making it possible to store the unique codes generated in memory, to generate unique codes for new liquids of a site of growth, harvest or conversion and to perform comparisons.

22 Claims, 7 Drawing Sheets

(56) References Cited

U.S. PATENT DOCUMENTS

| | | |
|---|---|---|
| 6,879,385 B2 | 4/2005 | Neda et al. |
| 8,906,405 B2 | 12/2014 | Shchepinov |
| 9,658,202 B2 | 5/2017 | Green et al. |
| 9,811,804 B1 | 11/2017 | Goenka et al. |
| 2006/0035382 A1 | 2/2006 | Shinozaki et al. |
| 2009/0042304 A1 | 2/2009 | Anderson et al. |
| 2009/0124019 A1* | 5/2009 | Ruiz Encinar ......... G01N 30/72 436/161 |
| 2010/0297774 A1 | 11/2010 | Green et al. |
| 2012/0323809 A1 | 12/2012 | Fukui |
| 2014/0328760 A1 | 11/2014 | Kruger et al. |
| 2018/0102240 A1* | 4/2018 | Bromage ........... G01N 33/1813 |
| 2020/0124585 A1 | 4/2020 | Fauvet et al. |

FOREIGN PATENT DOCUMENTS

| | | |
|---|---|---|
| EP | 1677105 | 7/2006 |
| GB | 2 320 960 A | 7/1998 |
| WO | WO 94/09618 | 5/1994 |
| WO | WO 2010/092202 | 8/2010 |

OTHER PUBLICATIONS

International Search Report dated Apr. 15, 2020 in International Application No. PCT/EP2019/087197.

* cited by examiner

ISOTOPIC MARKING AND IDENTIFICATION OF LIQUIDS

The present invention concerns the marking of liquids and by-products derived from processing (wines, spirits, sparkling wines, champagne, juices, syrups, concentrates, water, gelatine, milk and milk derivative products). It particularly concerns an isotopic method for identifying a liquid and by-products thereof, and a method allowing a unique, permanent identification code to be given to these liquids and their by-products. Finally, the invention concerns a data recording medium and an electronic computer to implement said method The possibility of determining the origin of liquids and their by-products has become a food safety challenge and a factor for market entry by winegrowers, farmers and processing industries in this sector. Winegrowing and farming unions, cooperatives, wine merchants and mass marketing are also increasingly concerned by issues relating to label of origin fraud, counterfeiting and food safety.

It is the objective of the present invention to propose a method with which it is possible, safely and reproducibly, to apply a unique code to a liquid and the by-products thereof, allowing identification of their origin and preferably with precision that goes as far as being able to identify the place of cultivation of the plant from which they are derived (examples: fruit juices including grape juice), the place of breeding of the animals from which they are derived (e.g. milk), the place of collection (examples: mineral waters and milk), places of production or processing (including vinification).

One particular objective is to provide an allocated unique code providing traceability at different levels of granularity e.g. of a vineyard, of a land parcel or designated place of origin, or much finer such as a vat and optionally vintage dating, which would also allow identification of possible fraud.

A further objective of the invention is to propose a safe and reproducible identification method of a liquid and its by-products allowing identification of the origin thereof and preferably with precision that goes at least as far as the place of cultivation, breeding, production or processing.

A further objective of the invention is to propose an identification method allowing characterization of product fraud, such as dilution, adulteration, blending, such action leading to a product which does not conform to its product description.

A further objective of the invention is to provide said methods adapted to the management of several or numerous estates or processing sites, and preferably with no limitation as to the number of estates and processing sites.

A further objective is to provide said methods which are economically viable.

SUMMARY OF THE INVENTION

These objectives and others are reached in particular through the use of a predefined model (M) used to give liquids and their by-products a unique isotopic code specific to an estate (e.g. vineyard, agricultural holding, or dairy farm), to a processing factory (e.g. milk derivative products) and optionally at even finer levels (e.g. vats, possibly the vintage), this code being based on the type and concentrations of chemical elements, or the concentrations or ratios of stable isotopes of chemical elements. These models can be improved by the measurement, knowledge and consideration given to concentrations of elements and/or isotopes of major elements contributed by nature (soils, water, incorporation by plants and animals) but also by man-operated processes, and able to provide a signature element that is predictable and can be analysed in the liquids.

As and when the solution is deployed to several estates or processing sites/factories, unique codes can be generated for each thereof, taking into account previously generated codes for other estates or processing sites/factories, optionally also with a notion of production cycle at the same estate or same processing site/factory. These unique codes are preferably generated per product type. As will be understood, it is also possible to reason in terms of generating unique codes for products which can then be controlled for authenticity with detection of possible fraudulent adulteration or tampering of the original product.

All these codes can be recorded in the model (M) preferably housed in an electronic computer or the like. Each unique code corresponds to the element and isotope signature of the liquid such as it is to be found up until the end of consumption thereof. This code can be given to the product at the time of production e.g. at the time of vinification or processing of the product and the by-products thereof. In the event of processing, it is advantageous to retain the element and isotope signature at the last stage of production on and after which there is no longer any substantial variation in the composition of the dry matter, of the chemical elements and of the concentrations or ratios of stable isotopes, otherwise a correction must be applied as explained below. Once the code is determined and applied to the product, this code no longer varies after processing (e.g. after vinification, processing of milk and derivative products) unless a correction is applied, and therefore also marks the products derived from the liquids and by-products thus marked i.e. the end products (without significant impact by any ageing process, for wine for example) and packaged products.

The effect of accumulation of markers (added isotopes) is completed once integrated in the process. The invention therefore takes into account the major moment i.e. the marking cycle (isotopic integration of markers). It is also possible to give consideration to the time needed for homogenisation of the markers in a liquid. This homogenisation can have recourse to an instrument (injector, mixer, etc.) to accelerate the distribution, mixing, homogenisation of the markers within a production volume and production time.

This code is the result of isotope integration determined by the model (M) and applied by the site manager (e.g. Cellar Master, Head of processing) in accordance with guidelines given by the model. To arrive at this unique code during production, vinification or processing of a liquid, the model (M) can take into account the integration or accumulation rate (AR) of the elements and/or isotopes in the liquid as a function of the isotope addition process and processing of the product.

The time of integration in the process can be an additional safety factor. For example, this integration can be made in one or several times, or over a single period or several periods e.g. 2 or 3. It can be performed on initiation of vinification, before bottling or processing. For example, for wine, isotope integration can be performed at the most upstream point possible of the vinification process to guarantee against any risk of label of origin fraud (for example by blending with other wines at a later stage, by dilutions for spirits). This code can also integrate the markers or so-called major elements which vary according to cycles, batches, labels of origin or vintages depending on the type of liquid.

Parameters can be previously determined by tests, for example on a set of vats for wine.

The invention provides for the possibility of more than one unique code, or several usable identifiable fractions of a unique code in the end product, allowing traceability back to more information and in particular to successive operators in the production chain.

In one embodiment, incorporation at several stages (e.g. 2) allows the obtaining of several signatures (e.g. 2). Preferably, each incorporation allows the application of a specific code without the preceding or subsequent incorporation(s) substantially modifying this code (i.e. without harming the viability and recognition of the code). With this embodiment, it is possible to have an early code which can be found in the event of mixing or sale of a liquid to a third party. For example, a specific unique code can be first applied, in particular by the first producer, then at least a second specific unique code is applied by the same producer or a subsequent producer. Each of these two codes can be traced by means of the invention. To give examples: a winegrower then a distiller; a first winegrower then an assembler; a harvester then a processor.

Preferably and advantageously, the choice of elements and their isotopes and of their respective ratios determined by Model (M) for each estate or sub-assembly (land parcels) or processing entity (site, factory etc.) is based on the prior knowledge of what is called herein the basic geochemical signature (BGS) of a harvest (grape harvest or sub-assembly (land parcels) or of a processing entity. This BGS as described below is the knowledge of chemical elements, of stable isotopes of some elements, of their respective concentrations and/or ratios within an estate or its sub-assembly, or of a processing entity before application of the code by integration of an isotope solution. The model (M) can advantageously integrate the capability of defining an isotope solution allowing the application of said unique code, by varying the stable isotopes of elements contained in the BGS and the concentrations or ratios thereof. Preferably, this will be obtained by the model (M) in the most minimalist manner possible taking into account the cost/production mode of the isotopes/level of isotope enrichment/isotope strategy as a function of markets or availability of isotopes so that the integration cost of the isotopes is as low as possible. All these characteristics apply to the subjects of the invention described in more detail below. This model (M) will also make it possible, when needed, to link a liquid (e.g. wine, champagne, spirit or milk) with a vineyard or product derived from a determined processing entity via the analysis of concentrations or ratios of elements and stable isotopes, allowing the determination of a concentration or ratio profile of elements and stable isotopes in particular via mass spectrometry, and comparison thereof with the unique codes recorded in the model (M). Some elements and their isotopic distribution (concentrations or ratios of the following elements or their stable isotopes: C, H, O, N, S) vary throughout the year, for example as a function of contributions by soil, feed or water. With the invention it is also possible to determine the production cycle of a liquid or by-product from a sample thereof.

In the meaning of the invention, by by-product it is meant everything derived from a natural or processed liquid. It can be a derivative product (e.g. vinegar, oils or semi-liquid products such as dairy products including yoghurts, cheeses, cream or butters). The method of the invention can be applied to a liquid intended for human consumption, but not limited thereto.

Therefore, the subjects of the invention are in particular an isotopic identification method and a method allowing the application of a unique code, and an electronic computer.

The subject of the invention is therefore a method for applying a specific code to liquids from a place of origin or to by-products of this liquid, comprising:

taking into account the basic geographical signature (BGS) of the liquid or by-product thereof, comprising the ratios of stable isotopes of significant chemical elements for the liquid from a place of origin; in particular, this BGS comprises the chemical elements of at least 2, 3, 4, or the 5 chemical elements of group (1): C, O, N, H, S; this BGS may also comprise the ratios of stable isotopes of at least 1 to 10 other chemical elements;

adding to this liquid (in one or more times, hereafter called «initial addition») with this BGS at least 1 stable isotope of at least 1, 2 or 3 chemical elements, preferably elements contained in the BGS, by means of which a liquid is obtained having an isotopic signature with a modified isotope ratio compared with the BGS.

In one preferred embodiment, the BGS comprises chemical elements of at least 4, or better still the 5 chemical elements of group (1): C, O, N, H, S.

In one embodiment, the BGS comprises the ratios of the stable isotopes of at least 5, 10, 15, 20, 25, 30, or the entirety of the elements of group (2): Be, Al, Ti, V, Cr, Mn, Fe, Co, Ni, Cu, Zn, Ga, Ge, Se, Rb, Y, Zr, Nb, Mo, Rh, Pd, Ag, Sn, Sb, Te, I, Ba, Hf, Ta, W, Re, Ir, Hg, Ti, Si; and/or of at least 3, 6, 8, 10, or the entirety of the elements of group (3): Sr, B, Li, Ca, Na, Mg, K, F, P, Cl, As, Pb, Cd; and/or of at least 5, 8, 12, or the entirety of the elements of group (4): La, Ce, Pr, Nd, Pm, Sm, Eu, Gd, Tb, Dy, Ho, Er, Tm, Yb, Lu. Preferably, the elements of groups (2) and (3) are chosen.

In one embodiment, the stable isotope(s) added to the liquid are stable isotopes of at least 3 elements selected from groups (2), (3) and (4). In one embodiment, the stable isotope(s) added to the liquid are stable isotopes of at least 1, 2 or 3 elements of group (2), preferably at least 1, 2 or 3 elements of group (2') Al, Mn, Fe, Co, Cu, Zn, Mo, Sn, Ti, Si. Preferably, the addition is made to this liquid of at least 1 stable isotope of these at least 1, 2 or 3 elements.

The invention more particularly concerns the method allowing a specific code to be applied to liquids, preferably wines or spirits, from a place of origin, or to by-products of this liquid, method wherein the basic geographic signature (BGS) is provided for the liquid or the by-product thereof, comprising:

(i) the concentrations of at least 5, 6, 7, 8, 9, 10, 11, 12 or the entirety of the elements in group (3): Rb, Sr, B Li, Ca, Na, Mg, K, F, P, Cl, As, Pb, Cd;

(ii) the concentrations of at least 5, 10, 15, 20, 25, 30, or the entirety of the elements in group (2): Be, Al, V, Cr, Mn, Fe, Co, Ni, Cu, Zn, Ga, Ge, Se, Y, Zr, Nb, Mo, Rh, Pd, Ag, Sn, Sb, Te, I, Ba, Hf, Ta, W, Re, Ir, Hg, Ti, Si; and (iii) the concentrations of stable isotopes of at least 1, 2, 3, 4, 5, 6, 7, 8, 9 or 10 of the elements in this group (2);

the method comprising the addition to this liquid having this BGS of a known quantity of at least 1 stable isotope of at least 1, 2 or 3 chemical elements in group (2), after which a liquid is obtained having a determined isotopic signature with a modified isotope ratio compared with the BGS.

The BGS may also comprise the concentrations of the chemical elements of at least 2, 3, 4 or the 5 chemical elements in group (1): C, O, N, H, S.

The BGS particularly comprises concentrations of stable isotopes of at least 1, 2 or 3 of the elements in group: (2') Al, Mn, Fe, Co, Cu, Zn, Mo, Sn, Ti, Si.

Preferably, the addition is made to the liquid of a known quantity of at least 1 stable isotope of at least 1, 2 or 3 of the elements in group (2'): Al, Mn, Fe, Co, Cu, Zn, Mo, Sn, Ti, Si.

The BGS particularly comprises the concentrations of at least 1, 2 or 3 stable isotopes of at least 1, 2 or 3 of the elements Fe, Cu, Zn, Mo, Sn, Ti, Si.

Preferably, the concentrations are determined for the BGS of at least 2 stable isotopes of at least 1 element from among Fe and Zn. In particular, 56Fe and 57Fe, and/or 66Zn and 68Zn are measured. Preferably, adding an isotope to the liquid varies the concentration of 56Fe and/or 57Fe, and/or 66Zn and/or of 68Zn.

The BGS particularly comprises the concentrations of the elements Rb, Sr and B.

The BGS particularly comprises the concentrations of the elements Li, Ca, Na, Mg, K, F, P, Cl, As, Pb, Cd.

It is possible to finetune the signatures by measuring, for the above elements and in particular for a reasonable and sufficient number of elements, the concentrations of some or all of their stable isotopes. For example, this may concern measuring these stable isotopes for 1 to 10 elements in addition to those of group (2), selected in particular from among the major elements and/or elements in group (3). A number is considered sufficient if it provides a precise distinction or location for the type of product under consideration. Group (1) concerns the «major» elements. Knowledge of these major elements and their stable isotopes gives a relatively precise indication in particular of the geographic location e.g. region. Group (3) contains the major trace elements. Knowledge of these major trace elements and of their stable isotopes, combined in particular with the major elements, gives a finer indication of the geographic location e.g. local.

In one embodiment, the unique code further integrates the provision of stable isotopes throughout the production process. This means that the unique code adds the effect of the initial addition (or initial additions if added at several times) of isotopes to the original liquid, and the effect of subsequent provisions of isotopes in particular those provided by processing of the original liquid e.g. via cask wood for wines and spirits. In one embodiment, the unique code integrates the effect of removal of dry matter during the production process These subsequent effects can be quantified or modelled with sufficient accuracy.

Depending on different embodiments, the addition of isotopes can therefore be made:

For spirits, just before placing in casks or other ageing vessel, or just before bottling;

For wines, just after pressing and fermenting, in particular after clarification or filtering, or after a maturation period, or just before bottling;

For milk, marking the collection tank specific to a farm or common to several farms;

For Champagne, marking in the Liquor;

For syrups, marking in the vat after pressing and collection of the concentrate;

For processed products, at the time of initial mixing of all ingredients. This principle is preferred for all manufactured products.

In one embodiment, the unique code is defined by an electronic computer as a function of unique codes already generated and recorded and of the BGS of the liquid or its by-product, this electronic computer comprising a model (M) having in memory the unique codes already generated.

In one embodiment, the BGS is measured of liquids or successive by-products of same type and each time a unique code is defined for the liquid or by-product last analysed, a code which differs from the unique codes previously defined and recorded in the model (M).

A further subject of the invention is an isotopic identification method allowing a liquid or a by-product to be linked with a place of origin. The method may comprise:

a—in a sample of the liquid or by-product:
(a1) measuring the concentrations or ratios of stable isotopes characterizing a geographic origin; in particular these isotopes are isotopes of at least 2, 3, 4, or the 5 chemical elements of group (1): C, O, N, H, S, and/or of group (4): La, Ce, Pr, Nd, Pm, Sm, Eu, Gd, Tb, Dy, Ho, Er, Tm, Yb, Lu, and/or of group (3): Sr, B, Li, Ca, Na, Mg, K, F, P, Cl, As, Pb, Cd; locating precision, or granularity, is in principle greater the higher the number of isotopes in these groups that are measured for isotope ratios; and
(a2) measuring the concentrations or ratios of isotope ratios characterizing an original liquid or by-product thereof in sufficient or significant number, for example at least 5, 6, 7, 8, 9, 10, 15, 20, 25 chemical elements selected from group (2): Be, Al, Ti, V, Cr, Mn, Fe, Co, Ni, Cu, Zn, Ga, Ge, Se, Rb, Y, Zr, Nb, Mo, Rh, Pd, Ag, Sn, Sb, Te, I, Ba, Hf, Ta, W, Re, Ir, Hg, Ti, Si, and/or group (3): Sr, B, Li, Ca, Na, Mg, K, F, P, Cl, As, Pb, Cd, and/or group (4): La, Ce, Pr, Nd, Pm, Sm, Eu, Gd, Tb, Dy, Ho, Er, Tm, Yb, Lu; obtaining a profile of concentrations or ratios of these stable isotopes; in one embodiment, measurement is made of at least the isotope ratios of the elements of which the concentrations or ratios are varied for the type of liquid concerned, called imposed isotopes;

b—comparing this profile with profiles recorded in a predefined model (M) comprising profiles in memory in the form of unique codes of others, each being specific to a type of liquid or by-product of a place of origin, each unique code having been previously generated by the model (M) with a variation in isotopes of elements;

c—concluding that the liquid or by-product to be identified has a profile substantially equal to a recorded code and hence indicating a place of origin if, after comparison, the profile substantially corresponds to a recorded profile, and on the contrary concluding that the liquid or derivative by-product does not come from any place of origin having a code recorded in the model, or that the liquid has been adulterated.

In one embodiment, the method comprises the use of an electronic computer in which there are recorded the unique codes specific to other liquids from at least one other place of origin, and/or in which the BGS is entered of a liquid from a place of origin for comparison with recorded profiles.

In one embodiment, under (a1) the natural ratios of isotopes are measured of at least 5 of the elements from group (3): Sr, B, Li, Ca, Na, Mg, K, F, P, Cl, As, Pb, Cd and all the elements of group (1) C, H, O, N, S.

In one embodiment, under (a2) the ratios of imposed isotopes are measured of at least 3 elements from group (2): Be, Al, Ti, V, Cr, Mn, Fe, Co, Ni, Cu, Zn, Ga, Ge, Se, Rb, Y, Zr, Nb, Mo, Rh, Pd, Ag, Sn, Sb, Te, I, Ba, Hf, Ta, W, Re, Ir, Hg, Ti, Si, and group (4): La, Ce, Pr, Nd, Pm, Sm, Eu, Gd, Tb, Dy, Ho, Er, Tm, Yb, Lu.

The subject of the invention is particularly an isotopic identification method allowing a liquid or by-product, preferably wine or spirit, to be linked with a place of origin, the method comprising:
a—in a sample of the liquid or by-product, measuring:
  (i) concentrations of at least 5, 6, 7, 8, 9, 10, 11, 12 or the entirety of the elements in group (3): Rb, Sr, B Li, Ca, Na, Mg, K, F, P, Cl, As, Pb, Cd,
  (ii) concentrations of at least 5, 10, 15, 20, 25, 30, or the entirety of the elements in group (2): Be, Al, V, Cr, Mn, Fe, Co, Ni, Cu, Zn, Ga, Ge, Se, Y, Zr, Nb, Mo, Rh, Pd, Ag, Sn, Sb, Te, I, Ba, Hf, Ta, W, Re, Ir, Hg, Ti, Si, and
  (iii) the concentrations of stable isotopes of at least 1, 2, 3, 4, 5, 6, 7, 8, 9 or 10 of the elements in this group (2);
to obtain a profile of concentrations of elements and of stable isotopes;
b—comparing this profile with profiles recorded in a predefined model (M) having profiles in memory in the form of unique codes, each being specific to a type of liquid or by-product from a place of origin, each unique code having been previously generated by the model (M) with a variation in isotopes of elements,
c—concluding that the liquid or derivative by-product to be identified has a profile substantially equal to a recorded code and hence indicating a place of origin if, after comparison, the profile corresponds to a recorded profile, and on the contrary concluding that the liquid or derivative by-product does not come from any place of origin having a code recorded in the model, or that the liquid has been adulterated.

Preferably, in a sample of the liquid or by-product, the concentrations are also measured of at least 2, 3, 4, or the 5 chemical elements in group (1): C, O, N, H, S.

The BGS notably comprises concentrations of stable isotopes of at least 1, 2 or 3 of the elements in group (2'): Al, Mn, Fe, Co, Cu, Zn, Mo, Sn, Ti, Si.

Preferably, addition is made to the liquid of a known quantity of at least 1 stable isotope of at least 1, 2 or 3 of the elements in group: (2') Al, Mn, Fe, Co, Cu, Zn, Mo, Sn, Ti, Si.

The BSG particularly comprises the concentrations of at least 2 stable isotopes of at least 1, 2 or 3 of the elements Fe, Cu, Zn, Mo, Sn, Ti, Si.

Preferably, for the BGS, the concentrations are determined of at least 2 stable isotopes of at least 1 element from among Fe and Zn. Measurement is particularly made of $^{56}Fe$ and $^{57}Fe$, and/or $^{66}Zn$ and $^{68}Zn$. Adding isotope to the liquid varies the concentration of $^{56}Fe$ and/or $^{57}Fe$, and/or of $^{66}Zn$ and/or of $^{68}Zn$.

The BGS particularly comprises the concentrations of the elements Rb, Sr and B.

The BGS particularly comprises the concentrations of the elements Li, Ca, Na, Mg, K, F, P, Cl, As, Pb, Cd.

Other subject-matter will become apparent on reading the following detailed description.

DETAILED DESCRIPTION

Definitions

Unless otherwise stated, the generic name «place of origin» of a liquid or by-product will particularly comprise:
the winegrowing estate or agricultural holding producing the plant from which the liquid is derived and/or ensuring the production or processing of plant or liquid: for example vinification, breeding, assembling, ageing for wines and spirits; for example concentration, pressing, extraction, pasteurisation for fruit juices;
the breeder of animals from which the liquid (e.g. milk) is derived, and/or the place or factory for producing or processing dairy products: e.g. pasteurisation, sterilisation, concentration, production of yoghurts, cheeses, etc.;
the place of collection or operation (e.g. mineral waters).

By «sub-assembly of a place of origin», it is particularly meant a vineyard parcel, orchard parcel, assembly or sub-assembly of animals on a farm, or on a much smaller scale such as a vat, cask, tun, and any container used in the field of wines and spirits, the dating of vintages, etc.

Unless otherwise stated, the designation «place of origin» when used, will encompass the «sub-assemblies».

Unless otherwise stated, the generic name «production cycle» will include a cultivation cycle, animal breeding cycle, production cycle and/or processing cycle. In the particular area of wines and spirits, this production cycle can correspond to a vintage.

Unless otherwise stated, the designation «production cycle» when used fora liquid, will encompass the «by-products» of this liquid, hence products from processing, extraction etc. derived from the original liquid. Preferably processing is construed as preserving of dry matter and/or without exogenous supply of matter of which the isotopic contribution is unknown.

The objective of the invention is to apply a unique code to a product found on the market or intended to be marketed. This product can be an «original liquid» that is not or only scarcely processed such as grape juice or milk. Most often it is a «processed product» e.g. wine, milk of which the fat content has been adjusted or which is pasteurised, sterilised (UHT), or processed into cheeses, yoghurts and other dairy products. Therefore, the unique code is the one contained in this processed product when it has not been tampered with or adulterated and is found on the market.

By «ratios of stably contained isotopes» in an original liquid, it is meant the ratios of isotopes of chemical elements in the original liquid at the stage when these ratios no longer vary; in other words, the original liquid no longer has an isotope composition which varies (unless it is the subject of adulteration or tampering, which can be demonstrated by the method of the invention).

By «natural ratios of isotopes», it is meant the isotope ratios of chemical elements found in the liquids and processed products subsequent to the production process which particularly includes breeding, cultivation, harvesting or collection, and to processing, excluding voluntary additions of isotopes intended to finalise the unique code. For the latter the term «imposed isotope ratios» can be used.

Isotopic Identification Method

The isotopic identification method allows the linking of an original liquid with a determined place of harvesting or processing (place of origin), and/or the characterization of adulteration of tampering of an original product, and/or the demonstration of label of origin fraud, via analysis of concentrations or ratios of stable isotopes.

In particular, the method in a sample of the original liquid to be identified may comprise a step a—to measure the concentrations (C2) of chemical elements and/or stable isotopes of chemical elements. It is possible to calculate the ratios (R2) between elements or more particularly between stable isotopes of one same element or more. This allows a profile to be obtained of concentrations or ratios of these elements and stable isotopes, in particular via mass spectrometry.

It may also comprise at a step b-, the comparison of this profile with profiles recorded in a predefined model (M) having profiles in memory in the form of unique codes each one specific to a place of harvesting or place of processing, each unique code having been previously generated by the model (M) and uniquely applied to a place of origin through the addition of isotopic matter to these liquids so that, at the time of their processing the concentrations or ratios of these stable isotopes in derivatives are substantially identical to the unique code.

It may also comprise at a step c-, the conclusion that the liquid or product derived from a liquid to be identified has a profile that is substantially equal to a recorded code [min, max interval]) and also indicating the place of harvesting or processing or a sub-assembly of this place taking part in the processing of this liquid if, after comparison, the profile corresponds to a recorded profile, and if this is not the case drawing the conclusion that the liquid or product does not come from any place of harvesting/processing or a sub-assembly of the place of harvesting/processing having a code recorded in the model.

The expression is used of a profile substantially equal to a recorded code. Consideration is given to some variability in the signature at the time of analysis and to the degree of accuracy of measuring instruments. To take this variability into account, the unique codes are preferably generated taking this variability as an input datum to avoid possible overlaps when measuring between recorded profiles/unique codes. In particular an interval of 0.0001 to 10% is used, preferably 5, 4, 3, 2, 1, or 0.1%.

In the remainder hereof, the term sub-assembly of a place of harvesting/processing will not always be used at the same time as the term place of harvesting/processing but it is to be considered that it is included in the term place of harvesting/processing.

In the remainder hereof, the measurements of concentrations (C2) or ratios (R2) of elements or stable isotopes of one or more elements allow the obtaining of isotopic profiles in the form of isotope ratios in one same element, and also preferably ratios between chemical elements. Measurements are taken using reliable measurement methods for the elements under consideration (see below).

In particular, at step a-, the concentration of the following chemical elements is measured:
- at least 3, 4, 5, 10, 15, 20, 25, 30, or the entirety of the elements in group (2): Be, Al, Ti, V, Cr, Mn, Fe, Co, Ni, Cu, Zn, Ga, Ge, Se, Rb, Y, Zr, Nb, Mo, Rh, Pd, Ag, Sn, Sb, Te, I, Ba, Hf, Ta, W, Re, Ir, Hg, Ti, Si, and/or at least 3, 4, 5, 10, or the entirety of the elements in group (3): Sr, B, Li, Ca, Na, Mg, K, F, P, Cl, As, Pb, Cd; and/or
- at least 3, 4, 5, 8, 12, or the entirety of the following elements in group (4): La, Ce, Pr, Nd, Pm, Sm, Eu, Gd, Tb, Dy, Ho, Er, Tm, Yb, Lu and/or, preferably,
- at least 2, 3, 4 or the entirety of the elements in group (1): C, O, N, H, S.

Preferably, the predefined model (M) comprises the unique codes of other places of origin for similar products and/or the unique codes allocated to a given place of origin in relation to which it may be desired to verify the authenticity of a product or adulteration thereof. This model (M) therefore contains the unique codes, and hence the ratios or concentrations of a certain number of chemical elements or isotopes of a certain number of chemical elements. Evidently, the correlation must be sufficient between the chemical elements defining the unique codes recorded in the model and the chemical elements to be identified in the sample to be compared. For each type of product and/or the origin thereof it is possible to pre-select representative groups of elements of which the isotope ratios will be measured both to construct unique codes and to perform subsequent analyses.

The preferred modes for managing the elements and their ratios are described below, which combine measurements of some thereof preferably per harvesting or processing cycle, with variations of others in liquids or derivative by-products.

Preferably, this unique code for a place of harvesting or processing was determined by the predefined model (M), and applied to the natural or processed liquids or any derivative products through isotope addition such that that this code is integrated by the liquid or its by-product permanently or with known evolvement. In this manner, all the liquids and the processed liquids or by-products have this unique code, and the model M has in memory all the unique codes generated at a given time.

Preferably, step a-, for each chemical element for which the stable isotopes are considered, comprises the determination of variations of one or more minor stable isotopes in relation to the most abundant.

Preferably, the concentrations or ratios of isotopes are measured by mass spectrometry (MS). Particular use can be made of Inductively Coupled Plasma Mass Spectrometry (ICP-MS,) more particularly Multicollector-Inductively Coupled Plasma Mass Spectrometry (MC-ICPMS), or Isotope-Ratio Mass Spectrometry (IRMS), or any other technique allowing measurement of the concentrations of the sought chemical elements and/or the identification and measurement of elements and their stable isotopes, with their concentrations or ratios, expressed for example in ratios of minor stable isotope(s) in relation to the most abundant stable isotope in the sample. It is also possible to perform concentration analysis by Laser Ablation Inductively Coupled Plasma Mass Spectrometry (LA-ICP/MS) or Laser Induced Breakdown Spectroscopy (LIBS).

In particular, the method may comprise the use of a programmable electronic computer provided with a programmable logic unit, a data recording medium and a data exchange interface linked via an internal data bus. The electronic computer may also comprise a man-machine interface.

The method can therefore comprise the acquisition, by the electronic computer, of the values of concentrations (C2) and/or ratios (R2), in particular such as measured by MS and/or other method, forming the isotopic component signature of a liquid or of a by-product derived from this liquid, for which it is desired to know whether it comes from a place of harvesting or processing, from a sub-assembly of a place of harvesting or processing having a known unique code recorded in the electronic computer, and optionally to determine the exact origin and/or the conformity or adulteration thereof.

The computer can therefore also carry out comparison between the data acquired by the computer and the unique codes recorded in its memory. With this comparison, the computer can determine whether the acquired profile corresponds or does not correspond to a recorded unique code and in the first case outputting the identity of the place of origin, or else concluding that there is no correspondence or adulteration.

It is fully possible to identify adulteration by comparing the marking of a product of which the signature is known which should be identified, and the isotopic component signature measured on the inspected product. It is possible to go even further, for example with the known isotopic markers specific to a label of origin it is possible, by analysing these markers, to determine whether or not the inspected product indeed has the origin it claims to have.

Example of marking of spirits against fraud: Spirits such as bottles of cognac are regularly the subject of fraud by dilution with water, an agricultural alcohol or neutral equivalent. This alters the composition of the product and in most cases the end consumer is unaware thereof and pays the highest price. The anti-fraud method uses an isotope-doped solution allowing the marking, and subsequent identification via analysis, of a label of origin, a vineyard or specific vintage, and verification of any dilutions which may have been fraudulently carried out. By means of the isotopic solution (Unique Code) known in terms of element composition and concentration thereof, it is possible to estimate the dilution of a bottle of spirits by comparing the initial formula of the unique code with a sample derived from one same batch of marked bottles.

Other example: IGP wines (having protected geographical indication) are diluted/blended with wines produced by another country. The most recent example being rosé wine fraud in the south of France. The wines are bought in Spain and resold in France without mentioning the origin. Consumers are duped and pay for lesser quality than expected.

Anti-counterfeit marking: Grand Cru or top-quality wines are the subject of counterfeit on account of their high price. Retailers offer wines which do not correspond to the vineyard estate of origin while taking care to copy the vineyard label. The isotopic marking of wine on a vineyard estate allows irrevocable identification of whether the wine is or is not from the estate of origin. The formula of the unique code initially integrated in the vinification vat (advantageously, marking is applied most upstream of vinification, in general just after harvesting also to prevent risks of fraud). When inspecting a bottle of wine via a sample (using a Coravin™, an instrument allowing a bottle to be sampled without uncorking), analysis will reveal the isotopic composition and content thereof with reference to a unique code designating a place or vineyard in the database of unique codes.

Marking to prevent vintage fraud: Some vineyards, in particular champagne vineyards, produce vintages for some years. However, when a vintage has less success, some vineyards do not hesitate to change the year with reference to a vintage which did obtain some success, for better sale of their stock. The end consumer is deceived by this prohibited practice and pays a high price for a product that does not correspond to the claimed product. Isotopic marking will allow identification of the provenance of a wine, the vineyard, a land parcel, and recorded data on major elements such as C, H, O, N, S in the database will allow determination of a period of a production cycle. Isotopic variations in the major elements over time will be sufficiently discriminatory for precise dating of each cycle.

With regard to the acceptable degree of variation, each newly created unique code is defined over a range of values, or else the computer contains instructions to apply a certain level of variability for each isotope-analysed element which particularly takes into account the addition of markers as a function of type of liquid or by-product. Hence the presence in the computer of data related to liquids and derivative by-products. In general, the markers are found throughout the process irrespective of liquid type. The quantities of isotopes added throughout the processing of a natural liquid can be 1-5-10/1000 relative to the values finally measured. More precise data can be generated and recorded in the computer, these data possibly being derived from experimentation in particular experimentation at the place of harvesting or processing or at a sub-assembly. The term «substantially» used herein takes this variability into account, the method of the invention simply authorises variability which does not jeopardise either the generation of a unique code (with isotope-by-isotope variations) or the capability of efficiently comparing a measured signature in a sample with a unique code. «Substantially» in particular can means a difference of no more than 5, 4, 3, 2, 1, 0.5 or 0.1% for a concentration or ratio.

The invention allows identification of the origin of products derived from natural or processed liquids.

As will be seen below, the method can allow, and the computer can also be programmed to allow identification of the cycle at the place of harvesting or processing (date of production of a batch or vintage). In this case, measurements of the major elements and optionally of their isotopes (C, H, O, N, S) in the liquids or by-products at each cycle, which vary from cycle to cycle on account of variations in the liquids, are recorded cycle after cycle in the recording medium of the computer, and the computer is programmed so that it is able to compare the values of these major elements in a sample of a liquid or by-product, and to relate these with the values of major elements between different cycles recorded in the recording medium.

Method Allowing the Application of a Unique Code

The method allowing application of a unique code specific to liquids from a place of origin. This unique code is the combination of ratios of natural stable isotopes and ratios of imposed stable isotopes. This method is particularly adapted to implementation of the aforementioned isotopic identification method. In particular it can comprise:

i) analysis of the abundance of chemical elements and stable isotopes of one or more chemical elements a) in a liquid of at least one production cycle at a place of origin, or b) in a by-product of this liquid, to obtain the basic geochemical signature (BGS) of the liquid or by-product;

2i) selection of one or more, preferably several in particular at least 3 chemical elements having stable isotopes, preferably selected from among the chemical elements contained in the BGS or in the list given below;

3i) addition to the liquid of this production cycle or subsequent production cycles at the place of origin, of one or more stable isotopes of the selected chemical elements. This addition can be in the form of an aqueous solution, a solid formulation or any other form of isotope addition, comprising a determined quantity of one or more stable isotopes of the selected element (s), for example a mixture of these isotopes in determined abundance (e.g. ratios of the isotopes of one same element). This addition or this abundance is calculated (by the computer in particular) to allocate an isotopic code specific to the liquids or their subproducts from the place of origin.

This unique isotopic code comprises ratios of isotopes derived from the BGS (not concerned by the addition of isotopes and which are therefore not caused to vary), and imposed ratios of isotopes of elements (elements preferably contained in the BGS) resulting from the imposed addition of isotopes.

Step i)

If the original liquid is the end product itself, preferably analysis is made of the abundance of elements and/or of the stable isotopes conforming to characteristic a).

If the original liquid is processed by operations which substantially preserve the dry matter of the original liquid, e.g. concentration, dilution, vinification, etc., the concentrations and/or ratios are substantially constant between the original liquid and end by-product, and it is possible to proceed according to characteristics a) or b).

In one mode however, the liquid or its by-product may collect elements and/or isotopes throughout its production cycle, for example wine or spirits may acquire elements and/or isotopes from the receptacle in which they are contained e.g. cask in natural material (wood, etc.). In this case, it is possible to proceed according to characteristic a) or b), but taking a given time of the production cycle, preferably the end of this production cycle before possible marketing or storage in a container that is neutral in respect of exchange of elements and/or isotopes, for example at the time of bottling.

As a variant, which is of importance in the sector of wines and spirits, it is possible to avoid such measurement at the end of the production cycle. It can be carried out beforehand and in particular as soon as possible, as soon as a stable level of isotopes is reached after the addition of isotopes. Thereafter, consideration is given to the variations which will take place up until marketing. Therefore, these variations are known in advance and taken into account by the model. The model takes these into account by integrating the impact of these variations in the unique code. For example, if the cask contributes elements and/or stable isotopes of such and such an element in a known and analysable amount, the code integrates this element combining it with the isotopic signature reached at the time of isotope addition. This allows the preventing (or allows the tracing) of any adulteration of the liquid during processing thereof downstream of marking.

If the original liquid is processed using a process leading to removal of fractions of the original liquid and of some elements or stable isotopes, therefore modifying the concentrations or ratios of the original liquid, in this case, the model of the invention gives consideration thereto. It is then preferred to use characteristic b) and therefore to calculate the BGS of the by-product itself. As a variant, characteristic a) is used, but with knowledge of the mean impact of processing on the BSG, which is taken into account by the model.

The concentration of elements and/or isotopes in the liquids or derivative by-products is evidently related to the place of cultivation or harvesting, as resulting from soil elements and available run-off water. In one embodiment, for BGS definition, excluding any isotope addition, at a different production cycle or before the addition of isotopes, the liquids can be analysed for the concentration or ratios of elements and/or isotopes at each cultivation, harvesting or processing cycle. Preferably, for BGS definition, control analyses are also carried out at different steps of the processing operation on the liquids or derivative by-products to verify the presence of the isotopes that have been chosen to vary at another production cycle or at a subsequent step, and the concentration or ratios thereof.

The BGS can substantially correspond to the isotopic signature that a liquid or derivative by-product at a place of origin would have when produced or treated in the traditional manner of this place of origin without the operation of isotope addition.

Plants and animals may feed on minerals and water having an isotopic signature and/or an element signature particularly a major element signature which may vary throughout production cycles.

In this case, it may be desirable to have a unique code, or fraction of a unique code, that is valid for more than 1 production cycle. In this case, one or more regular analyses can be added (for example 1 per cycle, for concentration) of the soil and/or run-off water. The model can then take into account the ascertained variations, and can consider that they are insignificant for obtaining of the unique code or fraction thereof, or it can decide to add a correction to the isotope feed. Consideration can also be given to potential contributions by containers containing the liquids and by-products, such as wooden casks for wines and spirits.

Similarly, for the long- or medium-term management of original products from a place of origin, or to mark a vintage for example, consideration is given to variations brought by the soil and/or run-off water, or by a container (e.g. wood cask) measured as previously, to modify the unique code with regard to variable elements, in general the major elements, and to take into account these variable contributions and their impact on the original liquid or processed product giving consideration to the accumulation rate concerned.

Step 2i)

In one embodiment, enrichment of one or more isotopes, or depletion of one or more isotopes, or a combination of enrichment and depletion can be carried out, to compare with results which would be obtained without such modification on the liquids or processed by-products at a given cycle. Depletion of an isotope of an element is obtained by adding one or more other isotopes of this same element, which translates as a lowered ratio of the isotope which was not the subject of an addition.

It will be seen below that it is possible to measure the ratios of isotopes of a greater or lesser number of elements, in particular among elements allowing finer geographic distinction. The greater this number, the more the basic signature BGS already gives a high degree of precision of the place of origin, and the more it is possible to reduce the number of elements for which a modified isotope ratio is to be applied. This is why it is preferable to start with a variation of at least 1, 2 or 3 elements, but those skilled in the art will have fully understood that this number can be varied, and in particular this number can be increased to increase precision if needed.

Preferably, at step 2i, a time is defined at which the liquids or processed products receive the isotope addition, so as to obtain liquids or derivative by-products at the time of bottling or packaging that have acquired the unique code specific to the place of origin. This time is adapted so that the unique code is present up until the time of bottling or packaging. If more preciseness is desired, this time is preferably chosen according to the expected benefit e.g. the addition of markers at the most upstream point of the cultivation or harvesting process for wine, at the time of alcohol reduction for spirits, at the time of liquor integration for champagne, or at the time of vatting for milk.

Choice of Elements

Preferably, some elements and their isotopic distribution are associated with functions of location and/or cycle identification, or for some liquids with vintages. Therefore, some elements and their isotopic variations are related to a coarse geographic location (e.g. regional), others to a finer scale of location (e.g. place of cultivation or harvesting or a sub-assembly, land parcels, etc.), others to the cultivation or harvesting cycle. Finally, some elements and their isotopic ratios are markers which are caused to vary to finalise the unique code.

Natural isotopy allows regional geolocation. It is generally based on analyses of what are called the 5 major elements (C, H, O, N, S) and on interpretation of the concentrations and/or isotopic ratios using a suitable analytical instrument, preferably of IRMS type. The concentrations of these major elements (or the ratios of the isotopes of these major elements) are preferably all measured, or else at least 2, 3 or 4 depending on the fineness of the scale obtained for a type of original liquid. Preferably, it is chosen not to vary their concentrations or ratios to maintain their ability to indicate or mark a regional geographic location. These elements and their stable isotopes are then preferably part of the BGS.

The major elements (C, H, O, N and S) can also be production markers in that their concentrations and/or isotopic ratios vary with the soil, vegetation and run-off water, according to time of year and to variations in soil composition, vegetation and run-off water throughout the year. In one embodiment, the concentrations and/or ratios in vegetation and water are measured or are known for each cultivation, harvesting cycle, and the impact thereof on the isotopic signature of the liquid or derivative by-product at the time of bottling or packaging. This part of the signature contributed by C, H, O, N and S (or a discriminating sub-assembly of 2, 3 or 4) then makes it possible, on analysing the liquid or by-products, to trace back (in addition to the geographic origin, place of cultivation, harvesting or processing) as far as the cultivation harvesting or processing cycle, and more specifically the date of the batch, vintage depending on type of liquid. Vintage is a form of dating. For example, analysis of 2, 3 4 or preferably the 5 major elements will allow unique identification of the vintage. In particular, analysis of 2, 3, 4, or preferably the 5 major elements combined with the other elements of the unique code (or with the unique code not integrating the major elements) will allow unique identification of the vintage of a given vineyard. With regard to wines, it can therefore be considered that there is first a unique code allowing identification of one vineyard from among others, and secondly the major elements are able to relate a vintage with a vineyard. Preferably, it is cross-referencing between the two signature elements which contributes towards reliable identification of the vineyard and the vintage.

To provide an even more precise geographic origin and to work towards obtaining a signature including a finer geographic origin, in one preferred embodiment recourse is had to measurements of concentrations of elements and/or isotopes of elements able to sign a finer geographic origin than the major elements. These elements are those of the two other lists indicated above. In these lists, there are some elements such as Sr, B, Li, Ca, Na, Mg, K, F, P, Cl, As, Pb, Cd which allow discrimination between close, even adjacent geographic places. Preferably, these elements (all or a representative discriminating number thereof, in particular at least 5, 6, 7, 8, 9, 10, 11, 12 or all), are measured for concentration and preferably isotopy. Sr, B and Li are geographic trace elements, soil and water markers, and are found in vegetation (vines, fruits, grasses, all that is botany-related) in specific concentrations and ratios. Preferably the ratios of these 3 elements are also measured. Ca, Na, Mg, K, F, P and Cl are major trace elements brought by soil, vegetation and water. Preferably, it is chosen not to vary the concentrations or ratios thereof to maintain their ability to indicate or mark a fine geographic location. The same applies to the elements Sr, B and Li or the elements As, Pb and Cd. These elements, and optionally their stable isotopes are therefore preferably part of the BGS.

However, for true distinguishing of original or processed liquids from a place of origin or from a sub-assembly of a place of origin (for example derived from crops or harvests in one same locality, adjacent land parcels), the means of unique signature (called imposed signature) are constructed via trace elements (stable isotopes) of which the natural abundance will be doped/caused to vary. To do so, the ratios of some isotopes are varied, preferably of elements other than the major elements. It is chosen to vary the concentrations, hence the ratios of isotopes for a sufficient number of elements to allow discrimination, and a minimum number can be set or a total of 1, 2, 3, 4, 5, 6, 7, 8, 9 or 10 elements. Insofar as it is only possible to vary the isotopes for a restricted but sufficient number of elements, the other elements of groups (2), (3) and (4) can be maintained and measured for integration in the unique code. Advantageously, it is chosen to vary the ratios of isotopes of elements which are naturally present in the liquids from a place of origin (hence in the BGS).

Preferably, during a cultivation, harvesting or processing cycle, the method comprises at least one analysis of the isotope addition to detect any variation or drift in the abundance of the stable isotopes of the selected elements.

Preferably, the method comprises the use of an electronic computer in which there are recorded the unique codes specific to other places of origin, previously determined and recorded. The programmable electronic computer is preferably provided with a programmable logic unit, a data recording medium and a data exchange interface linked together via an internal data bus. The electronic computer may also comprise a man-machine interface.

Preferably, the data measured to determine the BGS of a place of origin are entered into the computer, the latter via its programmable logic unit being capable of determining the BGS or geochemical passport, which forms the starting reference basis for a given site. These data notably comprise:
  the results of concentration measurements of chemical elements;
  the results of concentration measurements of the stable isotopes of one or more elements;
  the results of ratio measurements of the stable isotopes of some constituent elements of the BGS;
  the choice of application of characteristic a) or b);
  data relating to the availability of various stable isotopes of various elements potentially contained in the BGS, chosen from the list of isotopes that can be varied;
  the costs of these isotopes; and/or
  discrimination between the 3 above-mentioned groups of elements, namely classification of the ratios for each of the groups separately.

In one embodiment, the computer stores data on accumulation rate (AR) of the places of origin and preferably has computing means allowing a correlation to be set up between a variation in element and isotope abundance and isotope addition, to obtain the unique code at the time of bottling or packaging of the crop, harvest or production respectively. RA is dependent upon the amount measured in vegetation, run-off water added throughout their natural production cycle, and the computer is able to take this into account to calculate the isotope addition to be made.

Preferably, the computer stores the BGS of the liquids or derivative by-products. It also stores the unique codes specific to other places of origin (of cultivation, harvesting, processing or other sub-assemblies) which were determined at a previous time. By means of its programming and recorded data and/or user inputs, the computer is able to calculate and propose a variation in abundance of isotopes to define the isotope addition, and the method for integrating this isotope addition (i.e. time in relation to date of bottling or packaging, even grape harvesting) to allocate to the liquids derived from a place of origin the unique code specific to the end product (e.g. before casking or at the time of bottling or packaging).

According to one advantageous characteristic, the computer integrates the unique code allocated to each place of origin, in particular it contains all the unique codes of the places of origin on which the model has been deployed. Each code is stored in the database and can be modified for updating or addition of information. This code is composed in particular of the BGS and imposed isotope variations. It can be integrated in what is termed the geochemical passport which may also comprise additional elements, the designation of label of origin, designation of a parcel, of a vineyard, type of vine, or any other specific information related to the liquids, isotope variations over the different cycles of cultivation, harvesting, processing, for example variations related to seasons in particular with isotopic variations in run-off water, whether or not organic approved, practices followed for cultivation, harvesting, processing, in general all elements referring to a given site. All these data can be consulted.

The required variations in isotope abundance to obtain the unique code can advantageously be minimal and a difference of between 1-/1000 to 3/1000 can be applied.

Preferably, the computer knows (since the user has entered these data) and takes into account one or more and preferably all the following variables:
  the plant origin from which the liquid or by-products are derived;
  the operational time to obtain a natural or processed liquid before bottling or packaging;
  the time of isotope addition;
  the contributions of stable isotopes by a container or a processing step.
It may also have knowledge of:
  the accumulation rate AR in liquids or derivative by-products under conditions of cultivation, harvesting or processing;
  the possible contribution of uncontrolled elements (e.g. during cultivation, open air harvesting, rain for plants);
  soil-related data (in particular for organic crops).

Once the characterization phase of the site has been completed and recorded in the computer, and before defining isotope addition and the time of this addition, it is advantageously possible to perform control analysis on the original liquids to verify that the BGS content of stable isotopes and their concentrations/ratios, remains valid.

In one embodiment, the unique code integrates an isotopic signature of several rare elements, in particular at least 5, 8, 12, or the entirety of the elements in group (4). It can be specified that these rare elements are chiefly associated with the geographic location of the places of cultivation, harvesting or processing, in particular at continent, country or regional level.

In one embodiment, the unique code integrates an element signature and/or isotope signature of one or more elements, in particular at least 5, 10, 15, 20, 25, 30, or the entirety of the elements in group (2), and/or at least 3, 6, 8, 10 or the entirety of the elements in group (3). This element signature relates in particular to the identity of a place of cultivation, harvesting, processing or the sub-assembly thereof.

Preferably, the unique code integrates an element signature and/or isotope signature of the elements C, O, N, H, S, which is particularly related via vegetation to the origin of the liquids and derivative by-products. Preferably they are not varied.

In one preferred embodiment, the unique code comprises concentrations of elements and/or stable isotopes of major elements namely C, O, H, N and/or S, obtained after measuring concentrations (C3) or ratios (R3) of these isotopes in a liquid or derivative by-product. The elements (C, H, O, N et S) are the so-called major elements. The level thereof can vary from one cycle to another, in particular throughout one same year, and this variation can be known (the concentrations are measured in batches, vats, casks, vintages or others) and taken into account in the unique code, providing traceability at different levels of granularity for example a place of cultivation or harvesting, or much finer such as labels of origin, type of vine, type of production and same batch (production cycle).

The computer may also comprise data relating to the concentrations (C3) or ratios (R3) of the major elements or of the major isotopes (C, H, O, N et S) in the liquids, and the translation thereof in terms of concentrations or ratios found in the end liquid products or derivative by-products at the time of bottling or packaging depending on addition or accumulation rate. The computer is capable of calculating predictable corrected values by correction via the accumulation rate in the animal or plant under consideration.

The electronic computer can also be parameterized with environmental, vine plant, soil measurement data, marking cycle data according to the type of liquid (wine, champagne, sparkling wine, spirit, milk and derivative products), geographical or reference nutritional element data. All these data allow the generating of a unique code adapted to the targeted site. It is also to be specified that the computer can advantageously be parameterized with known reference nutritional values, toxicity values and any other criteria allowing the defining of unique codes (and hence isotopic formulas and addition modes) avoiding the generation of invalid codes which deviate from these criteria.

The computer calculates and proposes variations in abundance of stable isotopes and/or isotope addition time to impart the unique code at the time of bottling or packaging. Preferably, the computer is programmed to determine these variations in abundance in optimised manner in terms of costs and/or availability of isotopes. The user is therefore able to record data relating to these variables of abundance, cost and availability, and to update these over time so that computer can best manage the defining of elements and isotopes to be varied, and hence the isotope addition to be made to a liquid. The criterion heeded by the computer at all times is to define the elements and their isotopes, the concentrations or ratios thereof, to define a new unique code differing from those already determined for other places of origin.

Preferably, to adjust the isotope ratios for isotope addition, the abundance of stable isotopes of the chemical elements is varied (or proposed to be varied by the computer), in accordance with the rules set forth above.

The following embodiments can be described, with a strategy for use of the elements according to vineyards, labels of origin and parcel size so that it is possible to guarantee long-term traceability.

1. Productions of liquids or derivative by-products in very large quantities (tens of millions of hectolitres of milk or derivative by-products from milk in particular). Trace elements are selected (among Zn, Se, Mo, Si, Ti, Sn, Fe, Cr) produced by centrifugation. Isotope content can be enriched or depleted, this latter solution being the most favourable from an economic viewpoint. Marking is preferably performed upstream of the processing operation.

2. Productions of liquids in very large volumes (thousands to millions of litres of wines, spirits, sparkling wines, champagnes). Trace elements are selected (among Zn, Mo, Si, Ti, Sn, Cr) produced by centrifugation. Isotope content can be enriched or depleted, this latter solution being the most favourable from an economic viewpoint. Marking is performed as a function of type of liquid (e.g. for spirits at the time of adding water to lower the alcohol content, for wines just at the time the grapes are macerating after harvesting, for champagnes in the champagne liquor, for sparkling wines just before bottling).

The key factors also retained are solubility and distribution of the elements according to liquid. Implementation is highly important since it guarantees the efficacy of marking achieved via the encoding of an aqueous solution. This allows optimisation of the use and quantities of stable isotopes required.

It is also possible to describe the following embodiments for liquids as a function of type and place of cultivation, harvesting or processing (vine, winegrowing and vinification, fodder, agriculture and milk treatment, market gardening, fruit, fruit treatment . . . )

The level of enrichment of the selected isotope will vary the natural abundance of the other isotopes of one same element. Analysis of the isotopic ratios of one same element will allow evidencing of the ratio to be used to determine the presence of the marker(s) and the concentration value thereof.

With knowledge of the various elements and isotope ratios, it is possible only to vary the ratios (and hence to provide the corresponding isotope ratios, enriched and/or depleted) of 1, 2, 3, 4, 5, 6, 7, 8, 9, 10 elements.

The isotopes can be provided in any known manner. Use can be made of chlorides, sulfates and oxides. Chlorides and sulfates are generally water-soluble. They can be added simply to the beverage water or to any other liquid. Oxides are generally solid but they may also be added to irrigation water or to any other liquid.

Preferably, the quantities of isotopes added to the liquids or by-products are within the limits authorised by Nutrient Reference Values (NRVs) and within the limits of toxicity values. The computer can therefore be programmed with these data on NRVs and limits not to be exceeded in terms of toxicity; these data are integrated in the calculations and recommendations output by the computer.

Preferably, the quantities of isotopes added to the liquids or derivative by-products are added taking into account the accumulation rate (AR) of this or these isotopes in the liquid as a function of the time chosen for the isotope addition process. As already seen, the computer can integrate this knowledge of AR and give consideration thereto as described.

In one embodiment, the liquids or derivative by-products are marked exclusively or essentially exclusively via isotope addition.

Preferably, the liquids from a place of origin are marked with isotope addition at a key step of the processing operation before bottling or packaging. The computer is able to propose an isotope addition method which is suitable for a label of origin, vine type or varieties of milk under consideration, etc. in accordance with product-specific criteria recorded in its programme.

The liquid, of known isotopic composition, can be used as all or part of an aqueous isotope addition intended for an original liquid managed by the model (M) of the invention. Therefore, in one embodiment of the method for applying a unique code to an original liquid from a place of origin, the required volume of isotope liquid or the required quantity of isotopes is added to the original liquid.

A further subject of the invention is a data recording medium. The recording medium can contain executable instructions programmed to implement a method conforming to the invention when these instructions are executed by an electronic computer.

A further subject of the invention is an electronic computer to implement or which can be used to implement the isotopic identification method of the invention. This computer can comprise a programmable logic unit and a data recording medium containing software instructions which, when executed by the logic unit, are adapted to implement steps for comparing a profile of concentrations or ratios of chemical elements and stable isotopes in a sample of liquid (bottle or pack containing a liquid or derivative by-product) in the form of concentrations (C2) or ratios (R2), with profiles recorded in the form of unique codes each being specific to a place of origin, and to determine whether the liquid product or derivative by-product has a profile substantially equal to a recorded code and therefore indicating the place of origin, or whether the liquid product or derivative by-product does not come from any place of origin recorded in the model, or further that the liquid has been adulterated. The data recording medium 4 particularly comprises in memory the unique codes of at least one reference liquid (particularly a wine or spirit), this unique code representing a label of origin, a vineyard and/or vintage and comprising for each reference liquid (particularly a wine or spirit) the concentrations of at least 5, 6, 7, 8, 9, 10, 11, 12 or the entirety of the elements in group (3): Rb, Sr, B Li, Ca, Na, Mg, K, F, P, Cl, As, Pb, Cd, and at least 5, 10, 15, 20, 25, 30, or the entirety of the elements in group (2): Be, Al, V, Cr, Mn, Fe, Co, Ni, Cu, Zn, Ga, Ge, Se, Y, Zr, Nb, Mo, Rh, Pd, Ag, Sn, Sb, Te, I, Ba, Hf, Ta, W, Re, Ir, Hg, Ti, Si, and isotope concentrations or ratios of at least 1, 2 or 3 of the elements in group (2'): Al, Mn, Fe, Co, Cu, Zn, Mo, Sn, Ti, Si. Preferably, it also comprises the concentrations (C3) or ratios (R3) of the major elements (C, H, O, N et S), and optionally the stable isotopes thereof.

The unique code recorded for the reference liquids particularly comprises concentrations of stable isotopes of at least 1, 2 or 3 of the elements in group (2') Al, Mn, Fe, Co, Cu, Zn, Mo, Sn, Ti, Si; preferably the concentrations of at least 2 stable isotopes of at least 1, 2 or 3 of the elements Fe, Cu, Zn, Mo, Sn, Ti, Si. In particular, it comprises the concentrations of at least 2 stable isotopes of at least 1 element from among Fe and Zn, in particular 56Fe and 57Fe, and/or 66Zn and 68Zn.

The unique code particularly comprises the concentrations of the elements Rb, Sr and B.

The unique code particularly comprises the concentrations of the elements Li, Ca, Na, Mg, K, F, P, Cl, As, Pb, Cd.

Other characteristics of the electronic computer were described above.

The computer may further comprise all the functionalities, devices and programming needed to carry out the tasks described herein and which are allotted thereto:

The computer is the guarantor of the integrity of the unique codes.

The electronic computer receives the input of results of concentration analyses (Geochemical passport).

All the geographic trace elements, ultra-traces, macro-traces and (micro) trace elements can be listed therein.

The computer also contains the logic and strategies applicable to type of breeding or harvest.

When determining the isotopic variations to be performed in relation to natural abundance on 1, 2, 3 or more elements, the computer ensures that the code is not already allocated.

If the code is already allocated, and according to the logic and strategies applicable to type of breeding or harvest, the computer will perform an additional variation as a function of a doping index (e.g. +1/1000) until it finds an available code.

Should there be a problem of availability, it will first verify the differentiating elements of the geochemical passport and take into account a value or several values which are added to the formula of the unique code. This makes it possible not to add more than three markers in general. It is preferred to have a minimum signature based on the variation of 3 isotopes.

Once the formula/unique code is generated, the code is recorded in the computer.

The invention will now be described in more detail with the aid of embodiments taken as nonlimiting examples and with reference to the appended drawings.

Figure 4:
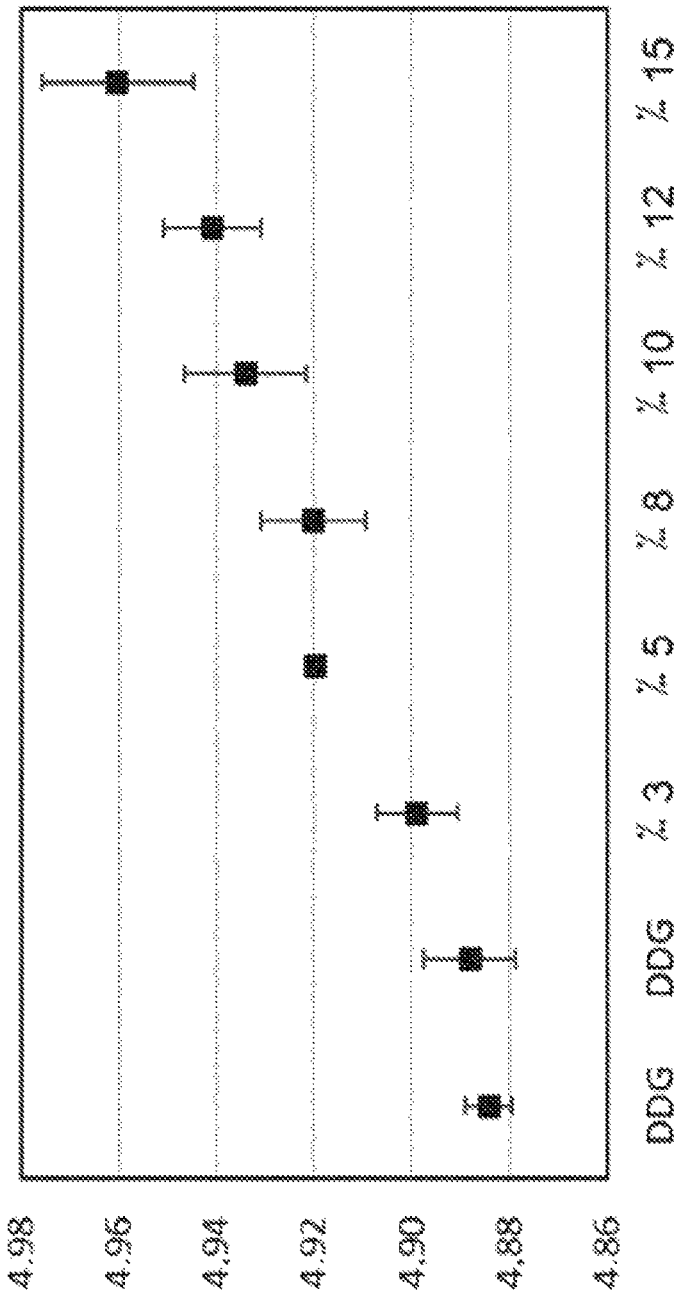

FIG. 4 is a graph showing the variations of the ratio 68Zn/67Zn in a wine as a function of 68Zn doping. X-axis: DDG is the name of the wine followed by indication of % doping with 68Zn. Y-axis: mass spectrometry value.

Figure 5:
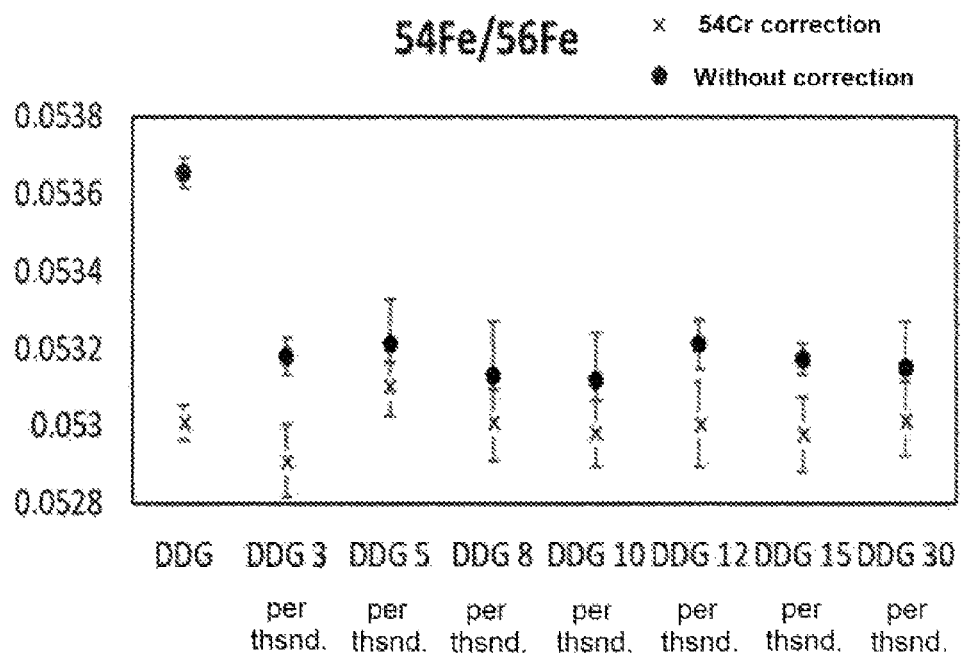
Figure 6:
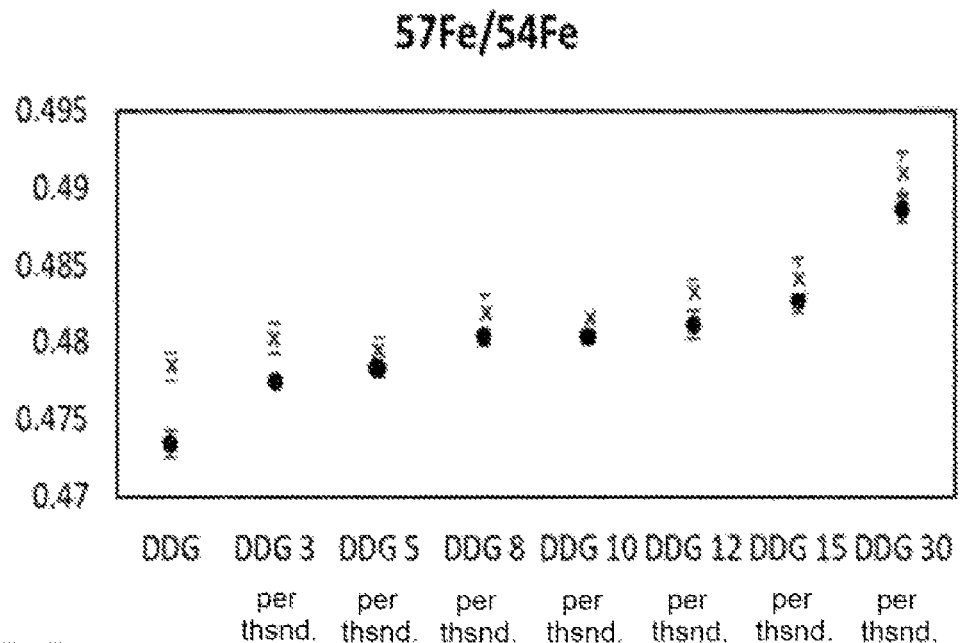
Figure 7:
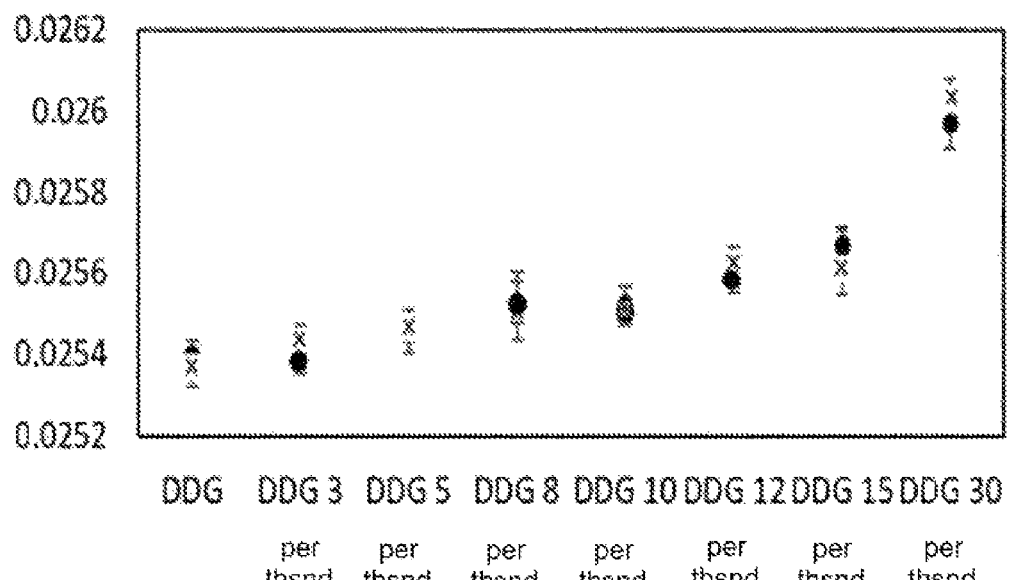

FIGS. 5 to 7 are MS graphs showing the trend in the isotope ratios 54Fe/56Fe, 57Fe/54Fe and 57Fe/56Fe with or without correction of interference between 54Cr and 54Fe, on samples of DDG wine, and as a function of performed isotopic doping (variation in the concentration of an isotope in relation to its reference natural abundance).

Figure 8:
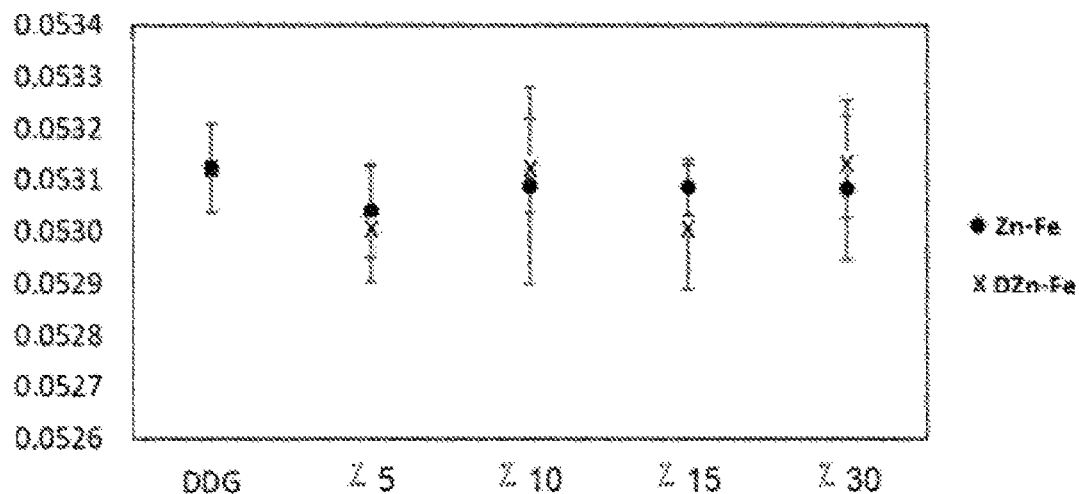
Figure 9:
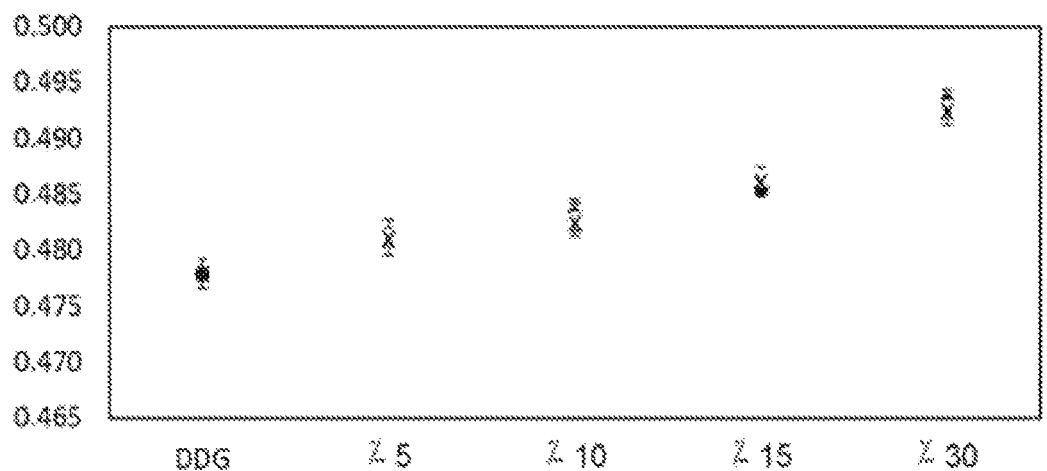
Figure 10:
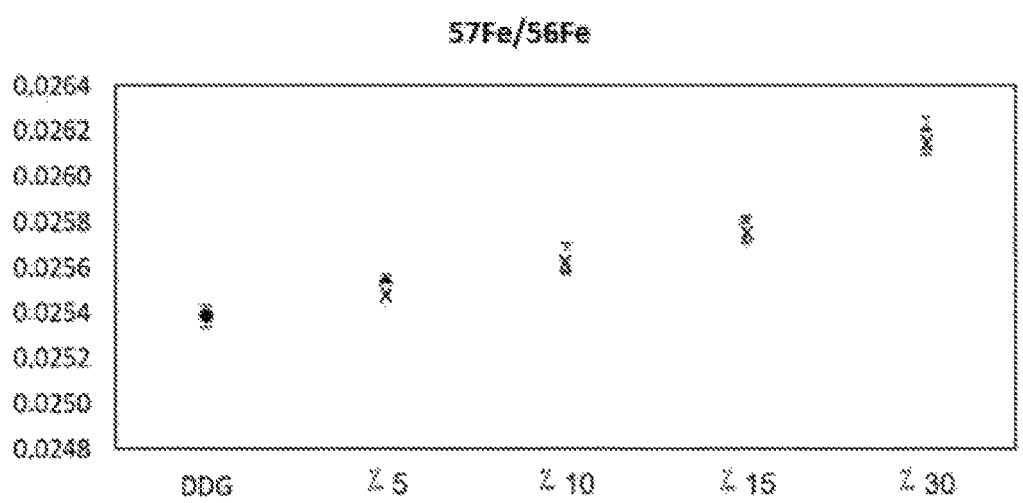

FIGS. 8 to 10 are MS graphs showing the trend in the isotope ratios 54Fe/56Fe, 57Fe/54Fe and 57Fe/56Fe, in samples of DDG wine, as a function of performed isotopic doping. Zn—Fe and de DZn-Fe are combinations of tracers (unique codes) allowing the demonstration that it is possible to mark/encode the same liquid with a different combination within the same range of values.

In FIGS. 5 to 10, the crosses are sometimes superimposed fully or partially over the black circles, which accounts for the fact that the circles are not or are only scarcely visible, but they are indeed present underneath the overlying cross.

EXAMPLES

Example 1: Description of a Computerized Assembly for Managing and Defining Isotopic Codes The assembly 1 comprises a programmable electronic computer 2 provided with a programmable logic unit 3, a data recording medium 4 and a data exchange interface 5 linked together via an internal data bus. The electronic computer 2 also comprises a man-machine interface 6.

For example, the unit 3 comprises a programmable microprocessor or microcontroller. The medium 4 here has a memory module e.g. of FLASH or EEPROM technology, or a magnetic hard disk. The medium 4 contains software instructions adapted to implement steps of the method in FIG. 2 when these instructions are executed by the computing unit 3.

The man-machine interface 6 here comprises a display screen, a data entry tool such as a keyboard and a loud speaker. As a variant, the man-machine interface 6 can be of different configuration.

For example, the electronic computer 2 is a microcomputer or mobile communication device such as a tablet or telephone. It can also be a remote computer server, accessible via the internet or a dedicated computer network. In this case, the interface 6 can be omitted and replaced by a dedicated communication interface e.g. a computer, communication device such as a tablet or television which fulfils the same functions as this interface 6 but is physically separate from the electronic computer 2.

In particular, the computer 2 is programmed to implement a predefined model M, for example by means of executable instructions stored in the medium 4.

The model M particularly allows the applying to liquids or derivative by-products of a unique isotopic code specific to a place of origin, and optionally at even finer levels of granularity (e.g. label of origin, type of vine, type of production and optionally batch), this code being based on the type, the concentrations or ratios of stable isotopes of chemical elements. In addition, the model (M) can when needed verify the relating of a liquid with a determined place of origin, via analysis of concentrations or ratios of stable isotopes, allowing determination of a profile of concentrations or ratios of these stable isotopes, in particular using mass spectrometry, and comparison with the unique codes recorded in the model (M).

The data used by the model M can be stored in the medium 4 and/or stored in a dedicated database accessible by the computer 2.

For example, the interface 6 is adapted to acquire input data e.g. in the form of digital or analogue signals or in the form of data structures such as values of accumulation rates AR and/or measurements of concentrations C2 and/or ratios R2 of stable isotopes. These data can also be transmitted to the computer 2 via the interface 6.

Figure 1:
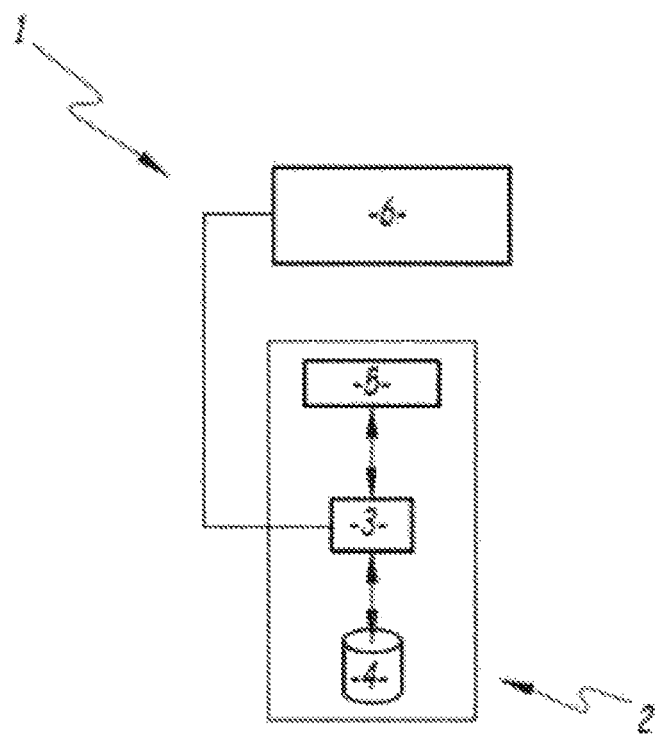
FIG. 1 is a schematic of an assembly with electronic computer able to be used to implement the invention.
Figure 2:
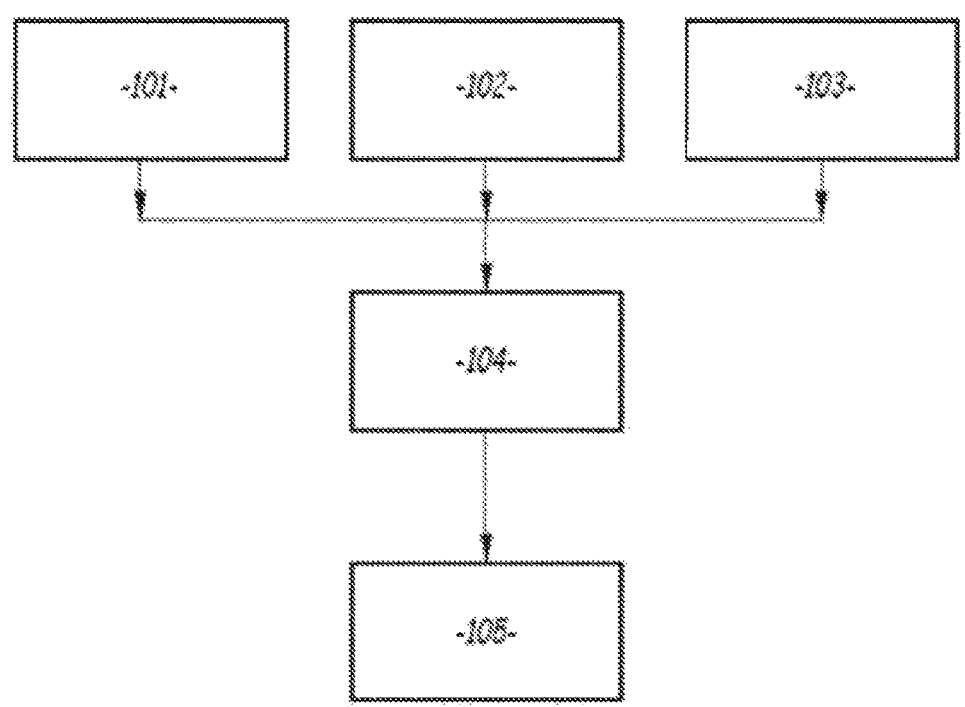
FIG. 2 is a flow chart of a method allowing a unique code to be applied to liquids.

FIG. 2, in connection with FIG. 1, schematically describes one embodiment of the method for applying a unique code.

MS is used to determine the BGS of the original liquid at step 101, the data are sent to the computer 2 e.g. via the interface 6.

The computer has in memory the unique codes which have been generated for other places of origin, this knowledge being identified at step 103 in FIG. 2.

By cross-referencing the data obtained at steps 101, 102 and 103, the computer at step 104 generates an isotope addition formula, which at the time of bottling or packaging, will allow liquids to be obtained having the unique code.

The addition method can be tested and the data held in the computer 2 for correlation between this operation and the obtaining of a stable isotope ratio of an element in a liquid or derivative by-product at the time of bottling or packaging. Adjustments (of content in particular) can be made to obtain usable isotope ratios i.e. with significant MS-measurable differences at the time of bottling or packaging.

The computer generates the composition of the isotope addition, to which the user has access via the interface 6 for example.

As a variant, the feed can be determined in advance and the computer gives the user the composition of the isotope addition.

Example 2: Application to a Red Wine Vineyard

Reference is made to FIGS. 1 and 2.

The BGS is determined of a liquid from a place of origin at step 101, the data are sent to the computer 2, for example via the interface 6. Samples of liquids are taken and analysed. The ratios of the stable isotopes of the following elements are determined (prior analyses determined the presence thereof at the place of cultivation, harvesting or processing, for example via mass spectrometry (MS) analysis on the liquid itself or on run-off water, soil, vegetation (vines, fruit trees . . . )):

these 26 elements: Li, Be, B, F, Na, Mg, Al, Ca, Cr, Mn, Co, Ni, Cu, Zn, Ga, As, Se, Rb, Sr, Mo, Rh, Pd, Ag, Cd, Te, Ba, Ti, Pb, Si, these 15 rare earths: La, Ce, Pr, Nd, Pm, Sm, Eu, Gd, Tb, Dy, Ho, Er, Tm, Yb, Lu.

The MS measurements in the invention in general, and in this particular example, can be performed with available methods, in particular:

Inductively Coupled Plasma Mass Spectrometry (ICP-MS),

Multicollector-Inductively Coupled Plasma Mass Spectrometry (MC-ICPMS)

Isotope-ratio mass spectrometry (IRMS).

LA-ICP/MS (Laser Ablation)

Laser Induced Breakdown Spectroscopy (LIBS).

The AR is known or can be calculated at step 102 by marking the liquids over a cycle with determined ratios of the stable isotopes of the indicated elements, followed by bottling or packaging, sampling the liquids or derivative by-products and MS analysis. The data are sent to the computer 2 e.g. via the interface 6.

The computer has in memory the unique codes which were generated for other places of origin, this knowledge is identified at step 103 in FIG. 2.

By cross-referencing the data obtained at steps 101, 102 and 103, the computer at step 104 generates an isotope addition formula and a treatment method which, at this place of origin, will allow liquids on bottling or packaging to have the unique code.

The addition method can be tested and the data held in the computer 2 for correlation between this method and the obtaining of a ratio of stable isotopes of an element at the time of bottling or packaging. Adjustments (of content in particular) can be made to obtain usable isotope ratios i.e. with significant MS-measurable differences at the time of bottling or packaging.

The computer generates the isotope addition composition and/or treatment method (operational process to be followed by the operator at the place of origin), which are accessible to the user via the interface 6 for example.

As a variant, the addition method can be determined in advance, and the computer provides the user with the composition of the isotope addition.

For liquids, it is therefore possible to define a method wherein the isotope addition forms the aqueous requirement in the week preceding bottling or packaging, step 105.

Example 3: Application to Wines Including Champagnes and Spirits

| Code | Label of origin | Year | Colour | Alcohol |
|---|---|---|---|---|
| CR | Côtes du Rhône | 2016 | Red | 13.5° |
| B1 | Bordeaux | 2015 | Red | 12.5° |
| B2 | Côte de Bourg Château Lallibarde (Bordeaux) | 2016 | Red | 13.0° |
| M | Muscadet Sèvre et Maine-sur-Lie | 2016 | White | 12.0° |
| AR | Alsace Riesling | 2016 | White | 12.0° |
| BA | Bourgogne Aligoté | 2016 | White | 12.0° |
| DG1-2 | Domaine des Gardes | 2015 | Red | 13.0° |
| R1-2 | Tain l'Hermitage | — | Red | 12.0° |
| CM | Champagne Mercier | — | Champagne | 12.0° |
| CBN | Champagne Alexandre Bonnet | — | Champagne | 12.5° |
| PSM | Cognac V.S Prince St Mérac | — | Cognac | 40.0° |
| VCC | Viognier, Caprice de Clairmont | 2016 | White | 13.0° |

Using mass spectrometry, with ICP/MS ICAP RQ spectrometer, and for each product in the above Table, the concentrations were determined of the chemical elements present, namely B, Na, Mg, Al, K, Ca, Mn, Fe, Cu, Zn, Rb, Sr, Li, Be, Sc, Ti, V, Cr, Co, Ni, Ga, Ge, As, Se, Y, Zr, Nb, Mo, Pd, Ag, Cd, In, Sn, Sb, Cs, Ba, La, Ce, Pr, Nd, Sm, Eu, Gd, Tb, Dy, Ho, Er, Tm, Yb, Lu, Hf, W, Hg, Tl, Pb, Bi, Th, U.

C, H, O, N, S can be additionally analysed for dating of the production.

In these winegrowing products, it can be seen that rare earths are practically non-existent. Su Among the elements Al, Mn, Fe, Co, Cu, Zn, Mo, Sn, Ti, Si, analysis first concerned Fe and Zn. Measurement was performed under conditions allowing measurement of concentrations of the isotopes 56Fe, 57Fe, 66Zn and 68Zn. The presence of these stable isotopes in all the samples and the distribution thereof allows the envisaged varying of the concentration of one in relation to the other and hence their ratios, in particular the ratios 56Fe/57Fe and 66Zn/68Zn, or the ratios of these Zn isotopes in relation to the majority isotope (64Zn) in natural abundance.

Figure 3:
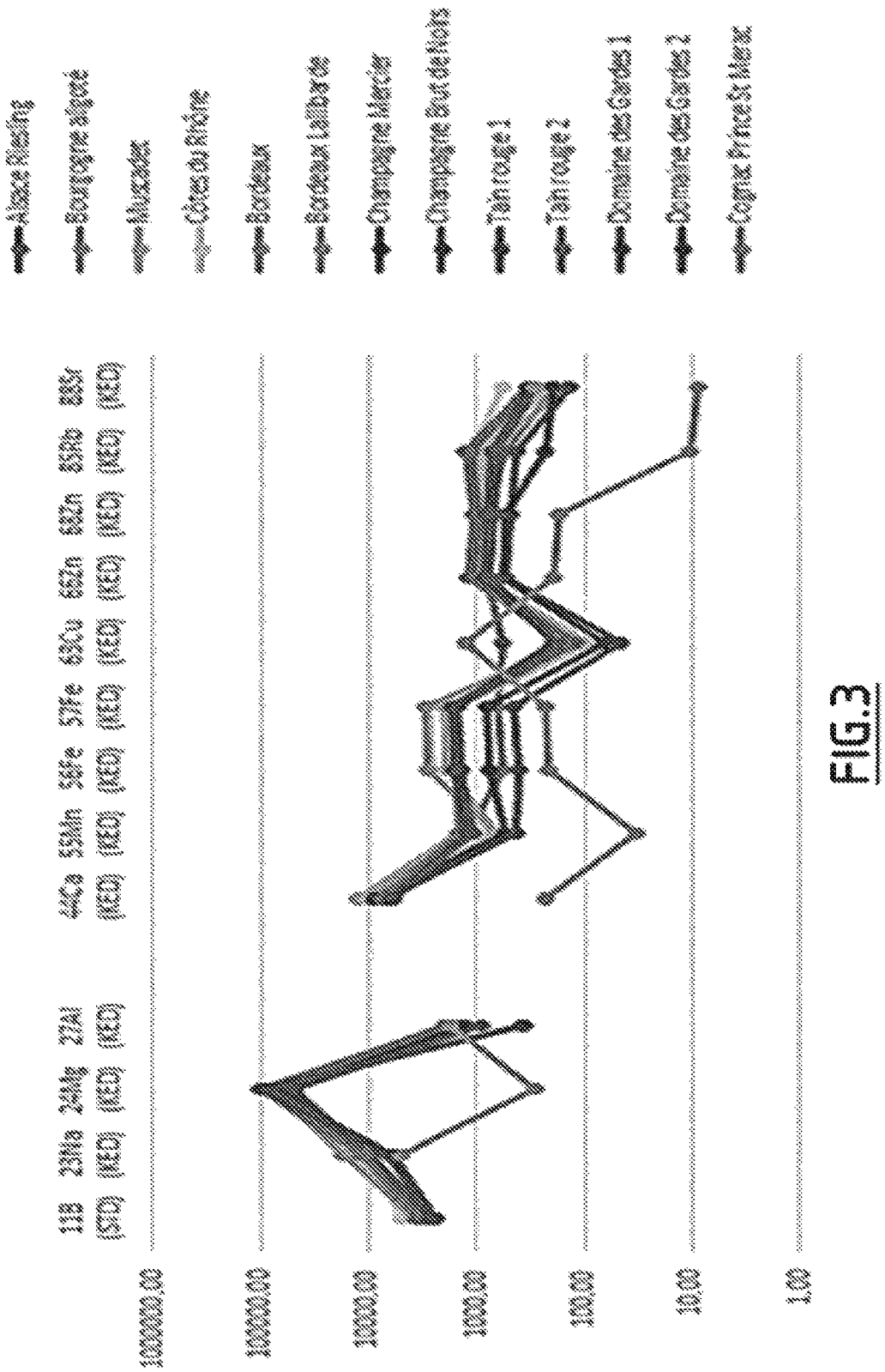
FIG. 3 is a graph extract showing, for different wines and spirits, the concentrations of the chemical elements B, Na, Mg, Al, Ca, Mn, Cu, Rb and Sr, and of the isotopes 56Fe, 57Fe, 66Zn and 68Zn, obtained by mass spectrometry. The interest of the graph is not the precise measured values but the fact that it shows that the values vary from one product to another.

The graph in FIG. 3 is an extract of the data obtained. The differences in concentration can be seen according to analysed product.

Variation in concentrations or ratios can be obtained in particular:
- By adding the isotope of which the concentration is to be increased.
- By adding the majority natural isotope.
- By adding a mixture of isotopes in natural abundance. Or
- By adding a mixture of isotopes depleted of the majority isotope.

A $1^{st}$ series was conducted to define the best procedures for preparing samples, based on analytical measurements of isotope ratios. The samples were white and red wines, Champagne, and a Cognac.

These marking tests were first performed on separate 10 ml wine samples, then reproduced on bottles. 68Zn isotope marking was applied to obtain a variation (doping) of 30‰ and higher, as a function of the initial Zn concentration. The samples were solely diluted, or mineralised and diluted before analysis. The dilution factor was approximately 20 and Zn concentration close to 50 ppb.

0.5 M $HNO_3$+In 1 ppb is the combination of an acid preparation composed of $HNO_3$+an inorganic acid In (of HCL type in very small amount 1 ppb)

Results:

The marked samples were compared with their reference samples (non-marked wines) following the equation:

$$\delta_{Zn}^{68} = \left[\frac{(68/67_{Marked\ wine})}{(68/67_{Reference\ wine})} - 1\right] * 1000$$

The analyses obtained with and without mineralisation globally showed the same results. Two test sessions were

|  | Tests 68ZN 0.95 ppm in solution | Volume | Results 68/67Zn | Volume | Results 68/67 | Results 68/66 |
|---|---|---|---|---|---|---|
| BA | Alsace Riesling | 59.8 µl | 39.4‰ | 48.2 µl (48.262) | 37.7‰ |  |
| M | Bourgogne Aligoté | 56.8 µl | 28.9‰ | 60.2 µl (60.168) | 27.0‰ |  |
| AR | Muscadet | 47.0 µl | 26.8‰ | 60.2 µl (60.168) | 26.1‰ |  |
| CR | Côtes du Rhône | 50.0 µl | 31.4‰ | 60.2 µl (60.168) | 30.8‰ |  |
| B1 | Bordeaux 1 | 59.4 µl | 29.7‰ | 60.2 µl (60.168) | 28.1‰ |  |
| B2 | Bordeaux 2 | 57.0 µl | 28.4‰ | 55.8 µl (55.786) | 28.7‰ |  |
| CM | Champagne Mercier |  |  | 33.4 µl (33.419) | 29.4‰ | 26.9 |
| CBN | Champagne A. Bonnet |  |  | 31.0 µl (31.082) | 29.4‰ | 29.1 |
| R1 | Tain 1 |  |  | 61.8 µl (61.754) | 27.0‰ | 26.9 |
| R2 | Tain 2 |  |  | 68.6 µl (68.554) | 30.4‰ | 30.1 |
| DDG1 | Domaine des Gardes 1 |  |  | 49.4 µl (49.344) | 33.7‰ | 30.9 |
| DDG2 | Domaine des Gardes 2 |  |  | 43.8 µl (43.807) | 26.8‰ | 25.9 |
| PSM | Cognac Prince St Méran |  |  | 10.8 µl (10.861) | 92.5‰ | High Eth = Low [Zn] = High ‰ |

Dilution of Wine Samples (without Mineralisation) for Analysis of Zn Isotope Ratios

| Samples (50 ppb in 10 ml) | Wine (ml) | 0.5 M $HNO_3$ + In 1 ppb | Measured concentration |
|---|---|---|---|
| CM | 0.899 | 9.101 | ~51 ppb |
| CBN | 0.966 | 9.034 | ~56 ppb |
| R1 | 0.486 | 9.514 | ~58 ppb |
| R2 | 0.438 | 9.562 | ~53 ppb |
| DDG1 | 0.609 | 9.391 | ~53 ppb |
| DDG2 | 0.686 | 9.314 | ~52 ppb |
| PSM | 2.765 | 7.235 | Ethanol interference | conducted. By default, liquids in principle do not need mineralisation for analysis, but to show the viability and coherency of results, we nevertheless verified liquid samples after mineralisation via an acid-based chemical preparation such as $HNO_3$, HCL, $H_2O_2$ ... ) allowing full solubility of the elements still present in the liquid.

$2^{nd}$ Series of Tests Performed on Bottles:

These analyses were performed to test the mixing of a drop (14.8 µl) of marked solution in a bottle of wine and Champagne (75 cl). 68Zn isotopic marking was applied to obtain a variation of 30% o and higher.

| | Red wine test | | | Champagne test | | |
|---|---|---|---|---|---|---|
| | Domaine des Gardes | | | Brut de Noirs, A. Bonnet | | |
| Zn concentration | 1141.4 ng/ml | | | 517.5 ng/ml | | |
| Volume 250 ppm $^{68}Zn$ | 14.8 μl | | | 9.4 μl | | |
| $^{68}Zn$ quantity | 3.516 μg | | | 2.215 μg | | |
| Wine (for dilution 10 ml) | 0.609 ml (50 ppb) | | | 0.966 ml (50 ppb) | | |

| | Sampling | $^{68}Zn/^{67}Zn$ | $\delta^{68}Zn$ | Sampling | $^{68}Zn/^{67}Zn$ | $\delta^{68}Zn$ |
|---|---|---|---|---|---|---|
| Natural | | 4.8786 | | | 4.8921 | |
| Glass 1 | +10 min | 4.9373 | 12.03‰ | +15 min | 5.6028 | 145.28‰ |
| Glass 2 | +10 min | 4.9348 | 11.52‰ | +15 min | 5.0626 | 34.85‰ |
| Glass 3 | +10 min | 4.9334 | 11.23‰ | +15 min | 5.0098 | 24.06‰ |
| Glass 4 | +2 h | 5.0424 | 33.58‰ | +1 h | 4.9838 | 18.74‰ |
| Last mixing | +2 h | 5.0606 | 37.31‰ | +1 h | 4.9819 | 18.36‰ |

$3^{rd}$ Series of Tests: Measurement of Standard Deviation on Unique Codes

Analyses of isotopic ratios with ICP-MS can show variations in standard deviation over several analyses. To create a differentiating unique code, we tested several codes for the isotope ratios Zn, DZn (Zn depleted of one isotope) and Fe. These tests were performed on 10 ml aliquots of the same wine DDG1 for variations (doping) of 3, 5, 8, 10, 12, 15 and 30% o.

| $^{68}Zn$ tracer | $^{68}Zn$ for 10 ml (0.5 ppm) | $^{68}Zn$ for 10 ml | $^{68}Zn$ for 75 cl | measured $\delta^{68}Zn$ % | Measured Zn concentrations |
|---|---|---|---|---|---|
| 0% | | | | | 46.27 ng/ml (0.41%) |
| 3% | 9.4 μl (9.375) | 4.69 ng | 351.57 ng | 2.80 | 45.30 ng/ml (0.48%) |
| 5% | 15.6 μl (15.625) | 7.81 ng | 585.96 ng | 4.46 | 45.66 ng/ml (0.60%) |
| 8% | 25 μl | 12.50 ng | 937.53 ng | 8.95 | 45.40 ng/ml (0.68%) |
| 10% | 31.2 μl (31.251) | 15.63 ng | 1171.91 ng | 9.67 | 45.39 ng/ml (0.72%) |
| 12% | 37.6 μl (37.50) | 18.75 ng | 1406.30 ng | 12.36 | 46.01 ng/ml (0.79%) |
| 15% | 47.0 μl (46.87) | 23.44 ng | 1757.87 ng | 16.35 | 46.15 ng/ml (0.99%) |
| 30% | | 46.88 ng | 3515.73 ng | | |

See FIG. 4.

Compared with the natural abundances of Zn, the 68ZnCl2 marker is highly enriched with 68Zn and depleted of isotopes 64, 66, 67 and 70 of Zn.

For the 67Zn/66Zn isotope ratio, the marker is non-observable. In the error bars, the results are the same.

For the 68Zn/67Zn isotope ratio, the values differ as a function of 68Zn marking. The two first values correspond to the DDG1 wine sample without marking. In the error bars, it will be easier to differentiate the 3‰ marking from the reference sample (not marked) with MC-ICP-MS.

Results of 57Fe Isotope Marking:

The isotopes analysed for our tests were 54Fe, 56Fe and 57Fe. 58Fe was not monitored on account of interference with 58Ni. 54Fe was also interfered by 54Cr.

For the 54Fe/56Fe ratio, the 57Fe isotope is not present and all the marking tests (5-10-15-20-25-30) can have the same error values. This is the case when the correction (54Cr) is applied to 54Fe. Without correction, these ratios have higher and differing values on account of the 54Ni signal.

Correction has no impact on the 57Fe/56Fe ratio. As with the Zn isotope ratios, distinguishing on 57Fe marking is possible for variations in marking of 5‰. For marking of 30‰ and higher, the error for Fe concentration is 1.5% RSD (Relative Standard Deviation, mean of isotopes 54, 56 and 57). For analysis of concentration, 56Fe is the recommended isotopic analysis, but 57Fe can also be analysed.

See FIGS. 5 to 10.

Both tests with the same DDG1 sample and the same quantity of marker allowed validation of reproducibility.

$$\delta^{57}_{Fe} = \left[\frac{(57/56_{Marked\ wine})}{(57/56_{Reference\ wine})} - 1\right] * 1000$$

Example of Marking and Unique Encoding of Domaine Des Gardes (One 10 ml Sample and One 75 cl Bottle).

| Tracer | $^{57}Fe$ for 10 ml (4 ppm) | $^{57}Fe$ for 10 ml (4 ppm) | $^{57}Fe$ for 10 ml (4 ppm) | $^{57}Fe$ for 10 ml (4 ppm) | $\delta^{57}Fe$ (%) (mean) |
|---|---|---|---|---|---|
| 3% DGG1 | 10.4 μl | 1.245 ng | 93.406 ng | (0.20%) | 2.98 ± 1.30 |
| 5% DGG1 | 17.4 μl | 2.076 ng | 155.676 ng | (0.20%) | 3.19 ± 1.14 |

-continued

| Tracer | $^{57}Fe$ for 10 ml (4 ppm) | $^{57}Fe$ for 10 ml (4 ppm) | $^{57}Fe$ for 10 ml (4 ppm) | $^{57}Fe$ for 10 ml (4 ppm) | $\delta^{57}Fe$ (%) (mean) |
|---|---|---|---|---|---|
| 8% DGG1 | 27.8 µl | 3.321 ng | 249.082 ng | (0.37%) | 6.37 ± 0.11 |
| 10% DGG1 | 34.6 µl | 4.151 ng | 311.352 ng | (0.35%) | 5.96 ± 4.40 |
| 12% DGG1 | 41.6 µl | 4.982 ng | 373.622 ng | (0.58%) | 10.10 ± 0.08 |
| 15% DGG1 | 52.0 µl | 6.227 ng | 467.028 ng | (0.63%) | 10.99 ± 0.42 |
| 30% DGG1 | 103.8 µl | 12.454 ng | 9 ng | (1.50%) | 26.26 ± 0.10 |

By comparing the analyzed/measured mass spectrometry values with the data stored in the database of the unique codes, we can precisely determine the place of origin of a wine. Analysis of enriched or depleted Zinc markers and of Iron markers allows the origin to be obtained with precision on a local scale, whilst minimizing the number of analyses to be performed.

With regard to corrections and isotopic interferences, it is possible to proceed in the two following manners:

Choice of a highly sensitive mass spectrometer, e.g. HR-ICP/MS Triple Quad combined with the use of helium.

The multi-element capacity and low detection limits of inductively coupled mass spectrometers, (ICP-MS) are major assets for the analysis of metals in trace form. However, the existence of polyatomic interferences can hamper this type of determination. The use of ICP-MS with a collision/reaction cell (CRC) allows such interference to be eliminated. Reactive gases are generally added but the use of a collision gas such as helium offers news prospects for the simultaneous elimination, with a single set of conditions, of all interferences in complex matrixes and of variable composition.

Preparation of an isotopic chemical separation allowing solely the elements to be analyzed to be isolated/retained. This preparation varies according to the elements used.

The invention claimed is:

1. A method of applying a specific unique code of a place of origin to a liquid or by-product thereof, said unique code comprising an isotopic structure;
wherein a basic geographic signature (BGS) is provided of the liquid or by-product thereof, comprising thirteen different elements as follows:
two elements of group (1) selected from the group consisting of C, O, N, H, and S;
five elements of group (2) selected from the group consisting of Be, Al, V, Cr, Mn, Fe, Co, Ni, Cu, Zn, Ga, Ge, Se, Y, Zr, Nb, Mo, Rh, Pd, Ag, Sn, Sb, Te, I, Ba, Hf, Ta, W, Re, Ir, Hg, Ti, and Si;
one element that is a stable isotope of one element of group (2); and
five elements of group (3) selected from the group consisting of Rb, Sr, B Li, Ca, Na, Mg, K, F, P, Cl, As, Pb, and Cd;
the method comprising adding to said liquid or by-product thereof having said BGS of a known quantity at least 1 stable isotope of at least 1, 2 or 3 chemical elements of group (2), wherein a liquid or by-product thereof is obtained having a determined isotopic signature, with a modified isotope ratio compared with the BGS.

2. The method according to claim 1, wherein the BGS comprises concentrations of stable isotopes of at least 1, 2 or 3 of the elements in group 2') Al, Mn, Fe, Co, Cu, Zn, Mo, Sn, Ti, Si.

3. The method according to claim 1, wherein the addition is made to the liquid of a known quantity of at least 1 stable isotope of at least 1, 2 or 3 of the elements in group (2') Al, Mn, Fe, Co, Cu, Zn, Mo, Sn, Ti, Si.

4. The method according to claim 2, wherein the BGS comprises the concentrations of at least 2 stable isotopes of at least 1, 2 or 3 of the elements Fe, Cu, Zn, Mo, Sn, Ti, Si.

5. The method according to claim 4, wherein, for the BGS, the concentrations are determined of at least 2 stable isotopes of at least 1 element from among Fe and Zn.

6. The method according to claim 5, wherein 56Fe and 57Fe, and/or 66Zn and 68Zn are measured and, via addition of isotope to the liquid or by-product thereof, the concentration is varied of 56Fe and/or of 57Fe, and/or of 66Zn and/or of 68Zn.

7. The method according to claim 1, wherein the BGS comprises the concentrations of the elements Rb, Sr and B.

8. The method according to claim 1, wherein the BGS comprises the concentrations of the elements Li, Ca, Na, Mg, K, F, P, Cl, As, Pb, Cd.

9. The method according to claim 1, wherein the unique code is defined by an electronic computer as a function of the unique codes already generated and of the BGS of the liquid or by-product thereof, this electronic computer comprising a model (M) having in memory the unique codes already generated.

10. The method according to claim 9, wherein the BGS is measured of liquids or successive by-products thereof, and each time a unique code is defined for the liquid or last-analyzed by-product thereof, this code differing from the unique codes previously defined and recorded in the model (M).

11. An isotopic identification method allowing a liquid or by-product thereof to be linked with a place of origin, the method comprising:
a—in a sample of liquid or by-product thereof, measuring thirteen different elements as follows:
two elements of group (1) selected from the group consisting of C, O, N, H, and S;
five elements of group (2) selected from the group consisting of Be, Al, V, Cr, Mn, Fe, Co, Ni, Cu, Zn, Ga, Ge, Se, Y, Zr, Nb, Mo, Rh, Pd, Ag, Sn, Sb, Te, I, Ba, Hf, Ta, W, Re, Ir, Hg, Ti, and Si;
one element that is a stable isotope of one element of group (2); and
five elements of group (3) selected from the group consisting of Rb, Sr, B Li, Ca, Na, Mg, K, F, P, Cl, As, Pb, and Cd;
to obtain a profile of concentrations of elements and stable isotopes;
b—comparing this profile with profiles recorded in a predefined model (M) having profiles in memory in the form of unique codes each specific to a type of liquid or by-product thereof from a place of origin, each unique code having been previously generated by the model (M) with a variation in isotopes of elements by carrying out the method according to claim 1; and c—concluding that the liquid or by-product thereof to be identified has a profile substantially equal to a recorded code and hence indicating a place of origin, if after comparison the profile corresponds to a recorded profile, and on the contrary concluding that the liquid or by-product thereof does not come from any place of origin having a code recorded in the model, or that the liquid or by-product thereof has been adulterated.

12. The method according to claim 11, wherein the BGS comprises concentrations of stable isotopes of at least 1, 2 or 3 of the elements in group (2'): Al, Mn, Fe, Co, Cu, Zn, Mo, Sn, Ti, Si.

13. The method according to claim 11, wherein the addition is made to the liquid or by-product thereof of a known quantity of at least 1 stable isotope of at least 1, 2 or 3 of the elements in group (2'): Al, Mn, Fe, Co, Cu, Zn, Mo, Sn, Ti, Si.

14. The method according to claim 12, wherein the BGS comprises the concentrations of at least 2 stable isotopes of at least 1, 2 or 3 of the elements Fe, Cu, Zn, Mo, Sn, Ti, Si.

15. The method according to claim 14, wherein, for the BGS, the concentrations are determined of at least 2 stable isotopes of at least 1 element from among Fe and Zn.

16. The method according to claim 15, wherein 56Fe and 57Fe, and/or 66Zn and 68Zn are measured, and via addition of isotope to the liquid or by-product thereof the concentration is varied of 56Fe and/or of 57Fe, and/or of 66Zn and/or of 68Zn.

17. The method according to claim 11, wherein the BGS comprises the concentrations of the elements Rb, Sr and B.

18. The method according to claim 11, wherein the BGS comprises the concentrations of the elements Li, Ca, Na, Mg, K, F, P, Cl, As, Pb, Cd.

19. The method according to claim 11, comprising the use of an electronic computer in which there are recorded the unique codes specific to other liquids or by-products thereof from at least one other place of origin, and/or in which the BGS is recorded of the liquid or by-product thereof from a place of origin for comparison with the recorded profiles.

20. An electronic computer that can be used to implement the isotopic identification method according to claim 11, comprising a programmable logic unit and data recording medium containing software instructions adapted, when executed by the logic unit, for implementing comparing a profile of concentrations or ratios of elements and stable isotopes in a sample of a liquid or by-product thereof, in the form of concentrations or ratios, with profiles recorded in the form of unique codes each one being specific to a place of origin, and to determine whether the liquid or by-product thereof has a profile substantially equal to a recorded code and hence indicating a place of origin, or whether the liquid or by-product thereof does not come from any place of origin having the code recorded in the model, or that the liquid or by-product thereof has been adulterated; the data recording medium having in memory the unique codes of at least one wine or spirit, this unique code representing a label of origin, a vineyard and/or a vintage and, for each wine or spirit, comprising the concentrations of thirteen different elements as follows:

two elements of group (1) selected from the group consisting of C, O, N, H, and S;

five elements of group (2) selected from the group consisting of Be, Al, V, Cr, Mn, Fe, Co, Ni, Cu, Zn, Ga, Ge, Se, Y, Zr, Nb, Mo, Rh, Pd, Ag, Sn, Sb, Te, I, Ba, Hf, Ta, W, Re, Ir, Hg, Ti, and Si;

one element that is a stable isotope of one element of group (2); and five elements of group (3) selected from the group consisting of Rb, Sr, B Li, Ca, Na, Mg, K, F, P, Cl, As, Pb, and Cd.

21. The method according to claim 1, wherein the liquid or by-product thereof is a wine or spirit.

22. The method according to claim 11, wherein the liquid or by-product thereof is a wine or a spirit.

\* \* \* \* \*